US006761902B2

(12) United States Patent
Sodroski et al.

(10) Patent No.: US 6,761,902 B2
(45) Date of Patent: Jul. 13, 2004

(54) PROTEOLIPOSOMES CONTAINING AN INTEGRAL MEMBRANE PROTEIN HAVING ONE OR MORE TRANSMEMBRANE DOMAINS

(75) Inventors: Joseph G. Sodroski, Medford, MA (US); Tajib Mirzabekov, Newton, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 09/749,240

(22) Filed: Dec. 27, 2000

(65) Prior Publication Data

US 2001/0034432 A1 Oct. 25, 2001

Related U.S. Application Data

(60) Provisional application No. 60/173,675, filed on Dec. 30, 1999, and provisional application No. 60/207,596, filed on May 26, 2000.

(51) Int. Cl.[7] ............................................... A61K 9/127
(52) U.S. Cl. ..................... 424/450; 264/4.1; 264/4.3
(58) Field of Search ................................ 424/450, 1.21, 424/9.321, 9.51, 417, 94.3; 436/829; 264/4.1, 4.3, 4.6; 428/402.2

(56) References Cited

U.S. PATENT DOCUMENTS

5,766,625 A    6/1998   Schreier et al.

FOREIGN PATENT DOCUMENTS

GB        2 135 647     *   9/1984

OTHER PUBLICATIONS

Sackmann Science 271, pp 43–48*, 1996.*
Bieri, C., (1999) *Nature Biotech*, 17:1105–1108.
Zhang, P. et al. (1998) *Nature*, 392:835–839.
Auer, M. et al. (1998) *Nature*, 392:840–843.
Mirzabekov, T. et al., *J. of Biol Chem.*, 274:28745–28750, 1999.

* cited by examiner

*Primary Examiner*—Goilamudi S. Kishore
(74) *Attorney, Agent, or Firm*—Nixon Peabody LLP

(57) ABSTRACT

A stable proteoliposome containing an integral membrane protein in a lipid membrane around an elliptoid or spherical shape. The shape preferably contains an attractant such as streptavidin or avidin and the lipid membrane contains a moiety that binds to the attractant such as biotin. The integral membrane protein is bound to a ligand which is anchored in the shape. Methods for making the proteoliposomes are provided. Kits for making the proteoliposome are described, as are the uses of the proteoliposome.

25 Claims, 19 Drawing Sheets

SCHEMATIC REPRESENTATION OF THE RECONSTITUTED gp 160 PROTEOLIPOSOMES

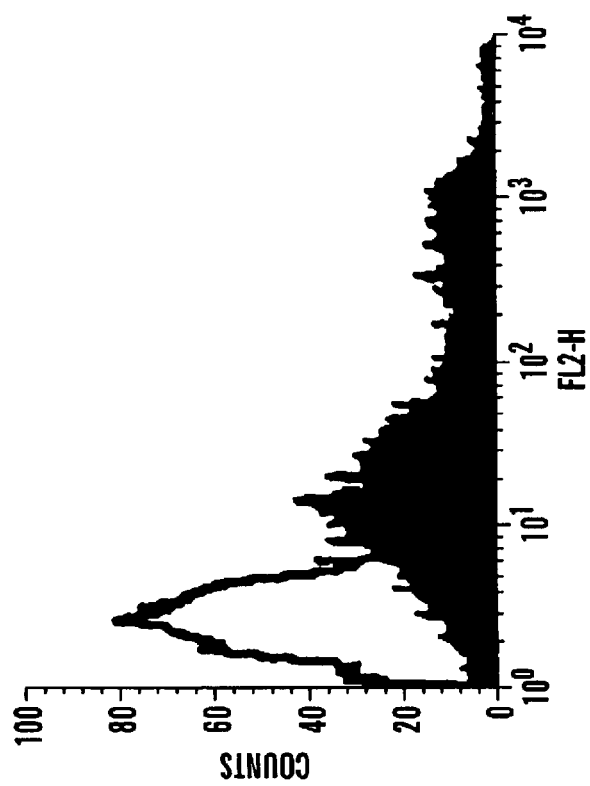
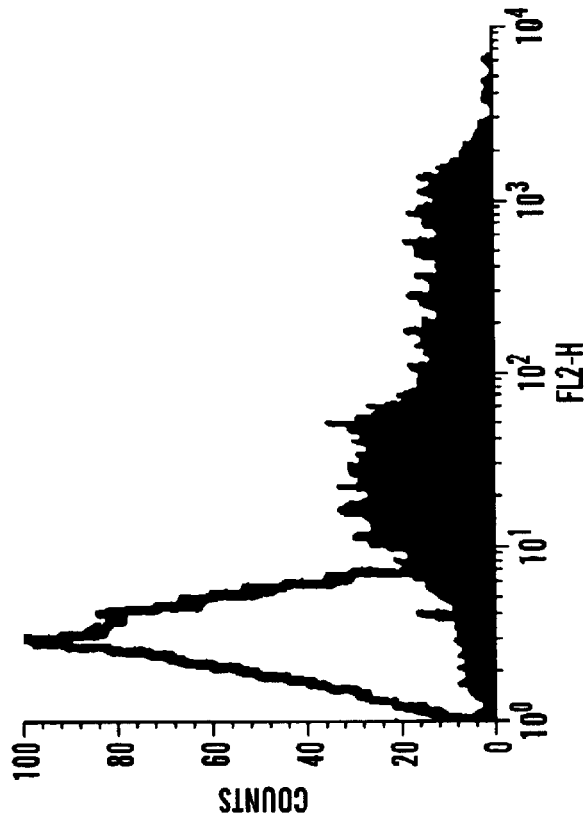
FIG. 15A
FIG. 15B

PROTEOLIPOSOMES CONTAINING AN INTEGRAL MEMBRANE PROTEIN HAVING ONE OR MORE TRANSMEMBRANE DOMAINS

CROSS-REFERENCE TO RELATED APPLICATIONS

This application claims priority under 35 U.S.C. §119(e) of U.S. Provisional Application Ser. No. 60/207,596, filed May 26, 2000, and U.S. Provisional Application Ser. No. 60/173,675, filed Dec. 30, 1999.

This invention was supported by National Institutes of Health Grant AI41851 and the government of the United States has certain rights thereto. ay 26, 2000.

FIELD OF THE INVENTION

The present invention is directed to proteoliposomes, their construction and use. Preferably the proteoliposome contains an integral membrane protein, having at least one transmembrane domain.

BACKGROUND OF THE INVENTION

Advances in genomics have resulted in the discovery and identification of numerous proteins. These advances have made it possible to obtain transcripts and DNA encoding a range of proteins, including putative integral membrane proteins having multiple transmembrane domains, as well as the proteins themselves. The availability of such proteins makes it possible to identify ligands that interact with these proteins, permitting one to better understand the biology of these proteins and/or screen for compounds that modulate the function of such proteins. However, there are increasing problems in knowing what a specific protein actually does and/or finding simple and accurate methods that actually identify the ligands that interact with a particular protein. For example, a protein such as a receptor protein for which a ligand has not yet been identified is referred to as an "orphan protein". Such orphan proteins are becoming more numerous as more DNA sequences, including DNA sequences encoding putative receptors, become available. In these cases, the DNA and proteins are classified based upon homologies to known proteins. For example, one can recognize conserved sequences that resemble a known domain, such as a transmembrane domain, thus indicating that the identified protein resides in a membrane (i.e., is an integral membrane protein).

Transmembrane proteins or integral membrane proteins are amphipathic, having hydrophobic domains that pass through the membrane and interact with the hydrophobic lipid molecules in the interior of the bilayer, and hydrophilic domains which are exposed to the aqueous environment on both sides of the membrane (for example, the aqueous environments inside and outside of the cell). The biological activities of integral membrane proteins (e.g., ligand binding) are dependent upon the hydrophilic domains; in some cases, the membrane—spanning regions contribute to function.

Despite our ability to predict extra-membrane protein regions with some confidence, the prediction of the actual structure of these regions and the ligands bound thereto is much more tenuous. For the most part, the identification of natural and unnatural ligands of integral membrane proteins is an empirical process.

The identification of ligands and the study of their binding properties is more complicated for integral membrane proteins than for water-soluble proteins. Water-soluble proteins can be readily purified in aqueous buffers and maintained in a native conformation under such circumstances. Integral membrane proteins cannot be solubilized in aqueous buffers but must be maintained in an environment that allows the membrane-spanning region to maintain hydrophobic contacts. This is most often accomplished by including detergents in the solubilization buffer. When mixed with integral membrane proteins, the hydrophobic regions of the detergent bind the transmembrane region of the protein, displacing the lipid molecules of the membrane.

Although solubilizing transmembrane proteins in detergents in theory allows their purification, in practice, it is typically difficult to effectively isolate that protein from other membrane proteins while retaining native conformation for extended periods of time. For example, the calcium pump from the sarcoplasmic reticulum can only be isolated with its native structure intact when maintained within the context of the sarcoplasmic reticular membrane (Zhang et al. (1998), Nature 392: 835–39). Similarly, a three-dimensional map of the plasma membrane H+-ATPase was only possible when two-dimensional crystals were grown directly on electron microscope grids (Auer et al. (1998), Nature 392: 840–3). For many other transmembrane proteins, including the cystic fibrosis transmembrane conductance regulator (CFTR), it has not yet been possible to purify the protein for extended periods of time while maintaining the wild-type conformation.

Additionally, identifying the actual ligands that interact with such a transmembrane protein, while extremely important, has many difficulties. For example, the transmembrane protein needs to be in the proper conformation in order to interact with ligands. Yet part of the way that transmembrane proteins maintain their conformation is by being part of a cellular membrane. The current solutions to this problem are less than optimal. For some integral membrane proteins that span the membrane only once, the extracellular and/or intracellular domains can be synthesized as independent entities and, in some cases, will fold properly. However, this is not always true. Furthermore, the post-translational modifications made to soluble versions of the extracellular or intracellular domains often differ from those of the full-length membrane-bound protein. These differences can exert profound effects on ligand binding or other functional properties. For the vast majority of integral membrane proteins, which span the membrane more than once, even this less-than-ideal solution is not feasible. Typically, cell-based screens are utilized to identify ligands of interest with these proteins. Cell lines that express the integral membrane protein of interest are established and compared to a parental cell line not expressing the protein. However, in such cases, it is difficult to effectively isolate the protein of interest from other proteins that are also present in the cell membrane. In many cases, the protein of interest is expressed in lower amounts than other integral membrane proteins. Thus, there can be interference caused by a compound or ligand interacting with an entirely different protein. For phenotypic screens, it may be that one protein is involved in one stage of a large pathway involving multiple proteins. In such cases, the readout in the screening assay may be affected even when the protein of interest is not directly affected. Accordingly, it would be desirable to have a method to look at a specific integral membrane protein in its native confirmation where it can be isolated from other competing proteins.

Seven-transmembrane segment, G protein-coupled receptors (GPCRs) represent approximately 1–2 percent of the total proteins encoded by the human genome and are important targets for pharmaceutical intervention. GPCRs have seven transmembrane domains, and also include chemokine receptors such as CCR5 and CXCR4, which have been identified as cofactors in permitting the human immunodeficiency virus (HIV) to enter cells. Generally low levels of expression and the dependence of the native conformation of GPCRs on the hydrophobic, intramembrane environment have complicated the study of these proteins. Analysis of ligand interactions with GPCRs and screening for inhibitors of such interactions are commonly conducted using live cells or intact cell membranes. Typically, the binding of radiolabeled ligand with the cells or the induction of intracellular calcium levels by the ligand are used as readouts in such screens. A significant drawback of such assays are the extremely large number of cells required for high-throughput screening. Furthermore, such studies can be complicated by the presence of numerous cell surface proteins, many of which are expressed at much higher levels than the GPCR of interest. Thus, certain approaches, such as using the GPCR-expressing cells to identify either natural or synthetic ligands in a complex mixture, are precluded. In addition, the generation of monospecific antibodies directed towards a particular GPCR in the complex cell membrane environment is inefficient. Furthermore, for some GPCRs, like the chemokine receptors, multiple ligands bind a single receptor, and conversely, a single ligand can bind multiple receptors. Therefore, if the cell expresses more than one receptor for the ligand being studied, interpretation of the results can be complicated.

Traditional methods of synthesizing and isolating a recombinant protein and then testing it in various assays have proven difficult with integral membrane proteins having multiple transmembrane spanning domains because they do not typically retain wild-type conformation under standard conditions for extended periods of time. For example, Bieri et al. (1997), *Nature Biotechnology* 17:1105–1108, used a sensor chip covered with a mixed self-assembled lipid monolayer to stabilize the G protein-coupled receptor (GPCR), rhodopsin. However, unlike most GPCRs, rhodopsin can be purified easily and its function is well-known. Moreover, it is expressed at high levels and is not denatured as readily in harsh detergents as other GPCRs. Even so, the protein was only stable for a number of hours. Further, the method used to detect the ligand it interacts with, surface plasmon resonance (SPR), looks at uncoupling of the ligands via changes in molecular weight of the ligand-receptor complex. If the ligand is roughly equivalent in mass to the G proteins, the loss of coupled G protein induced by the binding of a protein ligand would result in little overall change in the mass of the complex, and not be detected. Thus, for most GPCRs, establishing cell-free systems for screening for agonistic and antagonistic ligands remains an elusive goal.

Accordingly, it would be desirable to produce and isolate in purified form these multiple transmembrane domain proteins while retaining their wild-type conformation. It would be desirable if these proteins could be maintained in their wild-type conformation for extended periods of time and under conditions commonly found in vivo. It would also be desirable if this could be applied to a wide range of integral membrane proteins. The purification of integral membrane proteins, particularly those that span the membrane more than once, in a functionally relevant conformation should expedite the search for ligands, both natural and unnatural, that bind to these proteins.

SUMMARY OF THE INVENTION

We have now discovered a method for expressing integral membrane proteins in large amounts, purifying and isolating them from other proteins, while maintaining them in a wild-type conformation for extended periods of time.

Preferably, the integral membrane protein (sometimes referred to as a transmembrane protein) has a plurality of transmembrane domains. The known integral membrane proteins may cross the membrane only once or, for example, up to 16 times. One simple way to classify these proteins is by the number of transmembrane domains (Table 1, infra). Preferred proteins include G protein-coupled receptors (GPCRs), ion channels, amino acid transporters, glucose transporters, phosphate transporters, CFTR, and nuclear receptor complex proteins. Preferably, the proteins are eukaryotic, bacterial or viral membrane proteins; still more preferably the proteins are mammalian membrane proteins.

The desired protein is extended by a short peptide epitope tag, for example the C9 tag, which can be recognized by an antibody (for example, the 1D4 antibody). The tag can be added to the N-terminus or to the C-terminus of the protein, depending upon the ultimate orientation of the protein in the proteoliposome that is desired. The desired protein is expressed in a cell. Codon optimization may be used to increase the expression level of the protein. The protein is then isolated from the cell by a solubilizing agent that maintains the protein's conformation. Preferably, the solubilizing agent is a detergent. Preferred detergents include alkyl glucopyranosides (such as C8CP, C10-M, C12-M, Cymal-5, Cymal-6 and Cymal-7), alkyl sucroses (such as HECAMEG), digitonin, CHAPSO, hydroxyethylglucamides (such as HEGA-10), oligoethyleneglycol derivatives (such as C8ES, C8E$_n$ and C12E8), dodecylmaltopyranoside, and phenyl polyoxethylenes (such as Triton X-100).

The detergent-solubilized protein is then separated from the other cellular debris by capture onto a solid surface (e.g. a spherical or elliptoid bead). The bead has on its surface an antibody or other specific ligand that will capture, orient and concentrate the protein on the surface of the bead. This isolated protein is maintained in its wild-type conformation. Thereafter, it is mixed with a lipid component. One may also add an attractant for the lipid on the bead surface. For example, the bead can be streptavidin-coated and some lipid component (e.g. biotinyl-DPPE) can be covalently conjugated to biotin. The bead with the mixture is then subjected to a known means such as dialysis to form the proteoliposome. The streptavidin-biotin interaction, in this example, helps to attach the lipid layer to the bead surface as the detergent is removed. The resulting proteoliposome will maintain the integral membrane protein in its native conformation in an isolated and/or purified form for extended periods of times.

These proteoliposomes can be used as immunogens to elicit immune reactions. Alternatively, they can be used to screen antibody libraries for an antibody.

In a preferred embodiment, the stable proteoliposomes can be used as antigens to screen antibody libraries, including phage display antibody libraries.

These proteoliposomes can also be used in screening assays such as drug screening and identifying ligands.

These proteoliposomes can also be used to determine the protein's structure.

These proteoliposomes can also be used as a vaccine.

BRIEF DESCRIPTION OF THE DRAWINGS

FIG. 2A shows precipitates from cells lysed in buffer containing Cymal™-5, DHPC and Fos-Choline™-14. Similar levels of CCR5 were precipitated by the 1D4 antibody from these lysates, but the percentage of conformationally intact CCR5 varied (98% in Cymal™-5, 10% in DHPC, and 13% in Fos-Choline™-14). The sample run in the right-hand lane (asterisk) was the same as in the lane labeled 1D4 but was boiled prior to running on the gel, a procedure that results in the formation of high molecular weight multimers of CCR5. FIG. 2B shows the amounts of CCR5 precipitated by the 1D4 (○) and 2D7 (●) antibodies from cell lysates containing different detergents, over a range of pH values.

(FIG. 5B) The lipid membrane around CCR5-proteoliposomes was visualized by using the fluorescent lipid Rho-DOPE, which had been added at 1% concentration during proteoliposome formation. (FIG. 5D) CCR5-proteoliposomes were labeled with the anti-CCR5 antibody 2D7 conjugated with phycoerythrin (2D7-PE). In a control experiment, (FIG. 5C), CCR5-proteoliposomes were treated with an irrelevant antibody against CXCR4, 12G5-PE. Control beads with membrane only (FIG. 5E) and CCR5-proteoliposomes (FIG. 5F) were incubated with the JR-FL gp120-soluble CD4 complex, the C11 antibody against gp120 and goat anti-human IgG-FITC. Samples were analyzed using the Nikon Diaphot 300 Inverted Confocal Microscope and Oncor Image Software.

FIG. 6A shows reversible binding of the conformation-dependent antibody 2D7 to CCR5-proteoliposomes. CCR5-proteoliposomes were incubated for 1 hour at 22° C. with an irrelevant control antibody, IgG-PE (control), or with the phycoerythrin-conjugated 2D7 antibody against CCR5 (+2D7-PE). A fraction of the proteoliposomes with bound 2D7-PE was incubated for 15 minutes in 100 mM glycine-HCl (pH 3.0), washed twice in the same buffer, and then resuspended in FACS buffer (PBS+5% fetal cal serum) and analyzed by FACS (Wash). Part of these CCR5-proteoliposomes were again reincubated with 2D7-PE for 1 hour at 22° C. and analyzed by FACS. The results indicate essentially complete rebinding of the 2D7-PE antibody to the acid-stripped CCR5-proteoliposomes. FIG. 6B shows binding of $^{35}$S-cysteine/methionine-labeled gp120 to the CCR5-proteoliposomes. Equivalent amounts of $^{35}$S-cysteine/methionine-labeled gp120 glycoproteins from the CXCR4-using HXBc2 isolate or the CCR5-using ADA isolate were incubated with CCR5-proteoliposomes in the absence or presence of soluble CD4 (sCD4). In one experiment, the CCR5-proteoliposomes were incubated with the 2D7 anti-CCR5 antibody prior to incubation with the ADA gp120/sCD4 complexes. Proteins bound to the CCR5-proteoliposomes are shown, with molecular weight markers (in KDa) indicated on the left.

FIGS. 8A and 8C show cell surface expression of CCR5, with increased expression of CCR5 following sodium butyrate treatment of the cells (FIG. 8C). FIG. 8B shows expression of CCR5 in cellular lysates by immunoprecipitation, or by Coomasie Blue staining (FIG. 8D).

FIG. 12A shows FACS analysis of the proteoliposomes stained with antibodies, including AIDS patient sera. FIG. 12B shows analysis of protein content of the gp160 proteoliposomes on SDS polyacrylamide gels.

FIG. 14A shows FACS-generated binding curves of the IgGb12 antibody to gp160-expressing 293 T cells or to gp160-proteoliposomes. FIG. 14B shows FACS-generated binding curves of the antibody C11 to gp160-expressing 293 T cells or gp160-proteoliposomes Values were normalized maximal binding for comparison.

FIGS. 15A–B show FACS analysis of single-chain antibodies. Staining of 293T cells expressing gp160 is represented by the shaded peaks, and non-expressing control cells is represented by the unshaded peaks. FIG. 15A shows staining with polyclonal α-gp120 mouse serum and α-mouse-PE. FIG. 15B shows staining with bacterial medium containing phage/single-chain antibodies (1:2 dilution), α-phage mouse IgG and α-mousePE.

FIG. 17A shows autofluorescence. FIG. 17B shows gp160 proteoliposomes reconstituted with a lipid preparation containing 1% DOPE-Rhodamine.

DETAILED DESCRIPTION OF THE INVENTION

Figure 1:
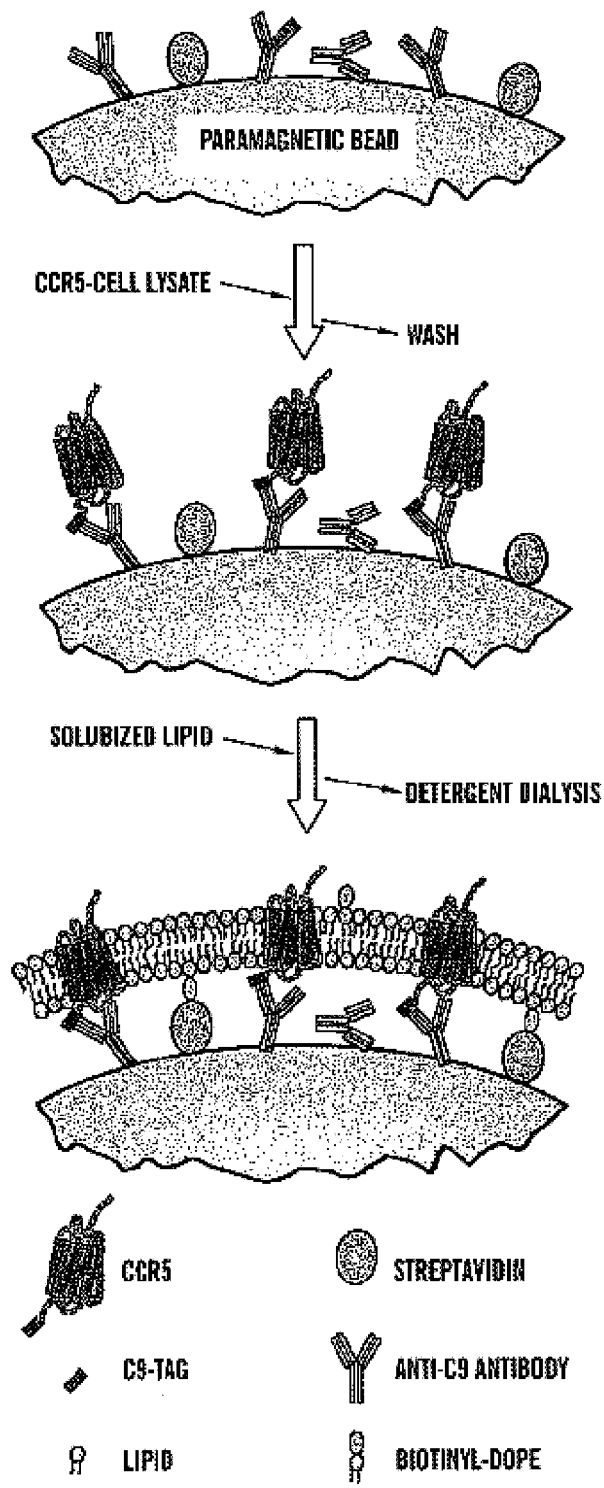
FIG. 1 is a schematic representation of the formation of a paramagnetic CCR5-proteoliposome. The surface of nonporous paramagnetic beads was covalently conjugated with streptavidin and an antibody that recognizes the genetically engineered C-terminal C9 tag on CCR5. The conjugated beads were used to capture the C9-tagged CCR5 from the cell lysate. After extensive washing, the beads were mixed with detergent-solubilized lipid containing approximately 0.1–1% of Biotinyl-DPPE. During the removal of detergent by dialysis, the lipid bilayer membrane self-assembles around the beads and CCR5 is returned to its native lipid environment.

We have now found a method for expressing integral membrane proteins in large amounts, purifying and isolating them from other proteins, while maintaining them in a wild-type conformation for extended periods of time. The protein of interest may be known to be an integral membrane protein or may be a putative integral membrane protein, based upon structure predictions from its distribution of hydrophobic amino acids. Preferably, the integral membrane protein has multiple transmembrane domains. More preferably, the protein has at least 3 transmembrane domains. Transmembrane domains have distinct and conserved characteristics. For example, the parts of the polypeptide chain that are buried in the hydrophobic environment of the cellular membrane (e.g., lipid bilayer) are composed largely of amino acid residues with nonpolar side chains. To span a membrane, each stretch of hydrophobic residues should be 10–25 amino acids long. The presence of such characteristic stretches of amino acids means that the general organization of a transmembrane protein can often be predicted from the distribution of its hydrophobic amino acids in a deduced amino acid sequence. In one embodiment, single domain proteins may form multimers (e.g. viral envelope glycoproteins). Thus, the resultant protein has complex conformational issues that are effected by the membrane. The present invention also works well with such multimeric proteins.

As used herein, an extended period of time is at least 12 hours; preferably at least one day; still more preferably at least one week. Even more preferably an extended period of time is at least one month. Yet more preferably, at least two months.

Any method of expression may be used to express the desired integral membrane protein in a cell, prior to its purification by the present invention.

The list of integral membrane proteins, sometimes also referred to as transmembrane proteins, is vast. Transmembrane proteins may cross the membrane only once or over twenty times. Many transmembrane proteins associate with other transmembrane proteins to form larger complexes. Such complexes may be comprised of two identical subunits (such as homodimers) or two different protein subunits (such as heterodimers). There are examples of even larger complexes of three (sodium ion channel, $Na^+/K^+$ ATPase), four (aquaporin), five (cation channels of nicotinic receptors, anion channels of glycine receptors) or more (photoreaction center, mitochondrial respiratory chain) homologous or heterologous subunits.

Transmembrane proteins contribute to a wide variety of cellular functions, including the transport of molecules and ions into or out of cells, cell recognition, cell-to-cell communication, and cell adhesion. One simple way to classify transmembrane proteins is by their number of transmembrane domains (Table 1).

The group of transmembrane proteins that only cross the membrane once (also known as single-pass proteins) is particularly diverse both structurally and functionally. This class includes a large number of cell surface receptor proteins. For example, the EGF receptor binds epidermal growth factor, which leads to activation of the receptor's tyrosine kinase activity. Other examples of single-pass transmembrane proteins include the integrins and cadherins, which function in cell-cell communication via binding to extracellular molecules.

Another large class of cell surface receptors is the G-protein coupled receptors (GPCRs), which span the membrane seven times. Unlike many of the single-pass receptors, these proteins do not have enzymatic activity themselves but instead are functionally linked to signaling proteins known as G proteins. The chemokine receptor CCR5 that serves as the principal coreceptor for HIV-1 is a typical example of a G protein-coupled receptor.

Other well studied members of this class include transducin, which senses light, and the acetylcholine receptor, which binds neurotransmitter at neuronal synapses.

Because of its hydrophobic interior, the plasma membrane is highly impermeant to most polar molecules including small molecules such as ions, sugars, amino acids, nucleotides, and many cell metabolites. Membrane transport proteins fall into two general classes: a) carrier proteins, which bind the specific solute to be transported and undergo a conformational change to allow its transit, and b) channel proteins, which allow specific solutes, most often inorganic ions, to cross the membrane when they are open and form a channel.

Well-studied carrier proteins include the ABC transporters (spanning the membrane 6 times), which bind solute as well as ATP and change conformation upon the hydrolysis of ATP to ADP. Many ion pumps are examples of gated carrier proteins, such as the 10-membrane spanning catalytic subunit of the calcium pump.

Ions also cross membranes in channel proteins, which are typically gated so that they only open in response to a specific signal (such as a change in membrane voltage). Examples include some potassium channels (e.g. the Kcs $K^+$ channel), which spans the membrane twice, and voltage-gated potassium channels such as the Drosophila Shaker protein (spanning the membrane 6 times).

In a preferred embodiment, the transmembrane proteins are envelope proteins. Still more preferably, the proteins are lentiviral proteins. The lentiviral proteins can include, for example, proteins from human immunodeficiency virus (HIV), feline immunodeficiency virus (FIC), or visna virus. Preferably, the transmembrane protein is comprised of multimers of the basic unit, such as the trimeric spikes formed by HIV-1 or HIV-2 envelope proteins.

The lentiviral protein is preferably from a primate lentivirus, still more preferably a human immunodeficiency virus (HIV-1), e.g. the HIV-1 gp120 or HIV-1 gp160.

Oligomeric complexes containing lentiviral proteins can include any lentiviral proteins and any proteins which bind lentiviral proteins. In another preferred embodiment, the proteoliposome contains the lentiviral envelope glycoprotein and a cellular receptor such as CD4. In a further embodiment, the proteoliposome contains the lentiviral envelope glycoprotein, CD4, and a chemokine receptor, such as CCR5 or CXCR4.

Other examples of viral envelope proteins include, for example, envelope proteins from filoviruses (such as Ebola virus), orthomyxoviruses (such as influenza virus), VSV-G, alpha viruses (such as Semliki forest virus and Sindbis virus), arena viruses (such as lymphocytic choriomeningitis virus), flaviviruses (such as tick-borne encephalitis virus and Dengue virus), rhabdoviruses (such as vesicular stomatitis virus and rabies virus), Moloney leukemia virus, HSV, VZV, Mumps virus, Rhinoviruses, Measles, Rubella, Arbovirus, Enteroviruses (such as Polio, Coxsackie, Echoviruses), Polio virus, Coxsackie B, A & Echovirus, Rhinoviruses, Hepatitis viruses, Norwalk virus, Astroviruses, Togavirus, Alphaviruses, Pestiviruses, Coronavirus, Parainfluenza, Mumps virus, Measles virus, Respiratory Syncytial Virus (RSV), Bunyaviridae, Reoviridae, Reoviruses, Rotaviruses, HTLV, Polyomaviruses, Papillomaviruses, Adenoviruses, Parvoviruses, EBV, CMV, Varicella Zoster virus, herpes viruses, and Pox viruses.

| Protein Class | Specific example | # TM domains | Reference |
| --- | --- | --- | --- |
| Receptor guanylyl cyclases | Sperm React receptor | 1 | MBOC pp. 759–60 |
| Receptor tyrosine kinases | EGF receptor | 1 | MBOC pp. 759–60 |
| Protein tyrosine phosphatases | CD45 | 1 | MBOC pp. 768 |
| Integrins | Alpha, beta chains | 1 | MBOC pp. 996–7 |
| Cadherins | E-cadherin | 1 | MBOC pp. 996–7 |
| Chemotaxis receptors | | 2 | MBOC pp. 775–6 |
| Some potassium channels | Kcs K channel | 2 | Doyle et al. |

-continued

| Protein Class | Specific example | # TM domains | Reference |
| --- | --- | --- | --- |
| Connexins | | 4 | MBOC pp. 959 |
| Photosynthetic reaction center | L, M subunits | 5 | MBOC pp. 498 |
| Some ABC transporters | | 6 | Reimann & Ashcroft |
| Voltage-gated $K^+$ channels | Shaker | 6 | Reimann & Ashcroft |
| G-coupled receptors | Transducin | 7 | |
| | Chemokine receptors | 7 | |
| | Acetylcholine receptor | 7 | |
| Ion pumps | $Ca^{++}$ pump catalytic subunit | 10 | MBOC pp. 516 |
| | $Na^+$—$K^+$ pump catalytic sub. | 10 | MBOC pp. 516 |
| CIC channels | CIC-1 of skeletal muscle | 11 | Valverde |
| ABC transporters | MDR ATPase | 12 | MBOC pp. 522 |
| | Peptide pump | 12 | MBOC pp. 522 |
| | CFTR | 12 | MBOC pp. 522 |
| Anion transporters | Band 3 protein | 14 | MBOC pp. |

MBOC: Alberts, B., et al. (1998), *Molecular Biology of the Cell*, $3^{rd}$ Edition, Garland Publishing, Inc., New York.
Doyle, D. A., et al. (1998), *Science* 280: 69–77.
Reimann, F., and Ashcroft, F. M. (1999), *Cur. Op. Cell Biol.* 11: 503–8.
Valverde, M. A. (1999), *Cur. Op. Cell Biol.* 11: 509–16.

Sequences of these proteins are widely available in the literature and from computer databases such as Genbank. Thus, one can readily obtain the gene encoding a particular protein of interest. This gene can be expressed by any known means. These include creating an expression cassette, where the gene is operably linked to a promoter. Other enhancing elements are known and may also be used. The codons used to synthesize the protein of interest may be optimized, converting them to codons that are preferentially used in mammalian cells. Optimal codons for expression of proteins in non-mammalian cells are also known, and can be used when the host cell is a non-mammalian cell (for example, insect cells, yeast cells, bacteria).

The gene is then introduced into a cell for the expression by known means. For example, they can include vectors, liposomes, naked DNA, adjuvant-assisted DNA, gene gun, catheters, etc. Vectors include chemical conjugates, plasmids, phage, etc. The vectors can be chromosomal, non-chromosomal or synthetic. Commercial expression vectors are well known in the art, for example pcDNA 3.1, pcDNA4 HisMax, pACH, pMT4, PND, etc. Promoters that can be used to express the gene are well known in the art. The promoter chosen are selected based upon the host cell which the protein is expressed in. These include cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV5 promoter and the herpes simplex tk virus promoter.

Preferred vectors include viral vectors, fusion proteins and chemical conjugates. Retroviral vectors include Moloney murine leukemia viruses. Other vectors include pox vectors such as orthopox or avipox vectors, herpesvirus vectors such as a herpes simplex I virus (HSV) vector (Geller, A. I. et al., (1995), *J. Neurochem*, 64: 487; Lim, F., et al., (1995) in *DNA Cloning: Mammalian Systems*, D. Glover, Ed., Oxford Univ. Press, Oxford England; Geller, A. I. et al. (1993), *Proc Natl. Acad. Sci.: U.S.A.* 90:7603; Geller, A. I., et al., (1990) *Proc Natl. Acad. Sci USA*

87:1149), adenovirus vectors (LeGal LaSalle et al. (1993), *Science,* 259:988; Davidson, et al. (1993) *Nat. Genet* 3: 219; Yang, et al., (1995) *J. Virol.* 69: 2004) and adeno-associated virus vectors (Kaplitt, M. G., et al. (1994) *Nat. Genet.* 8: 148).

The particular vector chosen will depend upon the host cell used.

The introduction of the gene into the host cell can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

An antigenic tag may be inserted in the protein to assist in its purification and in orienting the protein on the solid surface. Preferably, the tag is present at either the N-terminal end or the C-terminal end of the protein. The tag is preferably 6 to 15 amino acids in length, still more preferably about 6 to 9 amino acids. The tag is selected and its coding sequence inserted into the gene encoding the protein in a manner not to affect the overall conformation or function of the protein. Tags can include HA, polyoma, C9, FLAG, etc.

The integral membrane protein expressing cell is then lysed in a buffer with the appropriate detergent and protease inhibitors so the protein can be separated from other cellular debris by conventional means without harming the protein.

In general, due to their amphipathic properties, transmembrane proteins can be solubilized only by agents that disrupt hydrophobic associations and destroy the membrane's lipid bilayer. The agents typically used are small amphipathic molecules which tend to form micelles in water. Preferably, the agent is a detergent. When mixed with membranes, the hydrophobic regions of the detergent bind to the transmembrane domain of proteins, displacing the lipid molecules. The polar ends of detergents can either be charged (ionic) or uncharged (non-ionic). Although integral membrane proteins can be maintained in a native conformation in a detergent solution, over time many such solubilized proteins undergo denaturation and aggregation.

When a detergent is removed from a transmembrane protein-detergent complex in the absence of phospholipid, the membrane protein molecules usually denature, aggregate and precipitate out of solution. If, however, the purified protein is mixed with phospholipid before the detergent is removed, the active protein can insert into the lipid bilayer formed by the phospholipids. In this manner, functionally active membrane proteins can be reconstituted from purified components. An integral membrane protein properly reconstituted into its native lipid environment is stable for extended periods of time.

Additionally, a critical factor for maintaining a functional conformation of a membrane protein during its purification is the choice of detergent used to solubilize the protein. The detergent best suited for a given membrane protein is typically determined empirically. If the protein has been investigated previously, the literature will indicate successful detergents. Moreover, one can rely upon the results obtained with related proteins to determine detergents that will be successful with other proteins. Thus, research on a related protein indicates the type of detergent most likely to extract the protein in an active form.

Detergents can be generally classed, depending upon the nature of their polar end, into three groups: non-ionic, zwitterionic, and ionic. Strong ionic detergents (such as SDS) can solubilize most membrane proteins, but tend to unfold the protein in the process, making them less useful for reconstituting active conformations. In general, milder non-ionic detergents are preferred.

Detergents recommended for gentle solubilization of membrane proteins include alkyl glucopyranosides (such as C8-GP and C9-GP), alkyl thio-glucopyranosides (such as C8-tGP, C10-M, C12-M, Cymal-5, Cymal-6, and Cymal-7), alkyl sucroses (such as HECAMEG), digitonin, CHAPSO, hydroxyethylglucamides (such as HEGA-10), oligoethyleneglycol derivatives (such as C8E5, C8En, and C12E8), dodecylmaltopyranoside, and phenyl polyoxyethylenes (such as Triton X-100).

Preferred detergents include alkyl thioglucopyranosides, dodecylmaltopypanoside and phenyl polyoxyethydenes. More preferably, Cymal-5, Cymal-6, Cymal-7, HEGA-10, digitonin, CHAPSO, dodecylmaltopyranoside, and Triton X-100. Still more preferably Cymal-5, Cymal-6, Cymal-7, CHAPSO, and dodecylmaltopyranoside.

Commercial kits are also available to assist in choosing a detergent appropriate for a given membrane protein. For example, both Anatrace and Calbiochem offer a variety of kits containing mixtures of different detergents.

There are many known instances of detergents which have been successfully used to purify functionally active membrane proteins. For example, decylmaltoside was used to purify the $K^+$ channel (Ksc $K^+$) from *Streptomyces lividans,* allowing its structure to be determined by X-ray crystallography (Doyle et al., *Science* (1998) 280: 69–77). Cymal-5, Cymal-6, Cymal-7, CHAPSO and dodecylmaltopypanoside are preferred detergents for GCPRs, more preferably for chemokine receptors (Mirzabekov, T. et al. (1999), *J. Biol. Chem.* 274: 28745–50).

The cleared cell lysate containing all solubilized membrane proteins and other water-soluble cellular proteins can be separated from the other cellular debris by conventional means. For example using high speed centrifugation, such as 150,000×g. Antibodies directed against the epitope tag on the protein of interest are used to capture this protein from the cell lysate onto the solid support (e.g., beads). After binding of the solubilized integral membrane protein to the antibodies immobilized on the solid support, the solid support is washed. Thereafter the purified detergent-protein mixture is formed into a proteoliposome as described below.

The proteoliposome comprises a spherical or elliptoid shape such as a bead or other pellet. Preferably, the bead or pellet is at least about 15% the size of a eukaryotic cell; still more preferably it is at least about 20% the size of such a cell; and even more preferably it is at least about 25% the size of such a cell. The shape is three-dimensional so that it can be coated on all sides. However, there can be substantial variability in the exact shape used. The exact shape chosen will depend upon the way the proteoliposome is being used. Thus, in some embodiments flakes are preferable to beads, e.g., as an immunogen, in others, a thicker ellipsoid can be preferable.

The spherical or elliptoid shape, e.g. bead, is preferably coated with a substance that will help attract and anchor a lipid layer. However, this is not necessary. For example, one can use a compound such as streptavidin or avidin to coat the spherical or elliptoid shape such as a bead and add a small amount of biotinylated lipid to the lipid mixture. For example, one can use a head group-modified synthetic lipid, such as dipalmitoylphosphoethanolamine-N-Biotinyl (Biotinyl-DPPE) or dioleoylphosphoethanolamine-lissamine Rhodamine B (Rho-DOPE) in solution with lipids. Such a mixture will form a strong uniform coating with, for example, a streptavidin coated-bead.

The spherical or elliptoid shape (such as a bead) will also have an anchor ligand such as an antibody bound to it that will specifically bind either the antigenic tag or a known specific portion of the integral membrane protein that is to be bound to the bead, thereby orienting the protein. The lipid solution containing biotinylated lipid is added to the beads with the captured protein of interest. Thereafter, the detergent is slowly removed by known means. For example, by dialysis, for e.g., at least 24 hours. The resulting integral membrane protein-containing proteoliposome is stable for an extended period of time. As used herein, an extended period of time means at least 12 hours; still more preferably at least one day; even more preferably at least one week; still more preferably at least one month; and even more preferably at least two months. Not only will the protein retain its conformation in these proteoliposomes for long periods of time, but it will do so under a wide range of conditions, such as pH and temperature.

Preferably the spherical or elliptoid surface that is used is a magnetic bead. Magnetic beads are well known in the art and can be obtained commercially. For example tosylactivated Dynabeads® M-(Bikker, J. A., Trumpp-Kallmeyer, S., and Humblet, C. (1998) J. Med. Chem. 41, 2911–2927)0 (Dynal, Inc., Lake Success, N.Y.). These are particularly useful in assisting in the purification of the protein. One can use such proteoliposomes as intermediates and transfer the stabilized proteoliposome to another surface. For example, a flake. When using the proteoliposome for injection into an individual, it is preferable that the surface is made of a biodegradable material.

While the proteoliposome will typically contain only the integral membrane protein of interest, there are instances where one may want to use more than one protein. For example, the chemokine receptor CCR5 is known to cooperate with the single transmembrane-spanning protein, CD4, in interacting with the HIV gp120 protein. Thus, one can prepare proteoliposomes containing CD4 as well as the envelope glycoprotein. In another embodiment one can have both CCR5 and CD4 as well as the envelope glycoprotein. This can readily be done by tagging the proteins with the same epitope tag at the C-terminus and preparing beads with the appropriate tag-reactive antibody. Alternatively, the proteins can be tagged with different tags and one can prepare beads having mixtures of different antibodies. This would allow one to vary the ratios of the two proteins in the proteoliposome.

The integral membrane proteins used preferably have a plurality of transmembrane domains. Preferred proteins include GPCRs (such as chemokine receptors), ion channels, amino acid transporters, glucose transporters, phosphate transporters, transport ATPases, CFTR, and nuclear receptor complex proteins. Preferred ion channels such as potassium channels, calcium channels and chloride channels, aquaporin channels, intracellular organelle channels such as mitochondrial porin channel or VDAC, endoplasmic reticulum calcium channel, chloroplast porin channel, and the porin channels of bacteria. Preferably the proteins are eukaryotic, bacterial and viral membrane proteins. Still more preferably the proteins are mammalian.

In one embodiment there are kits that can be used to create the stable proteoliposomes. One preferred kit contains vials containing reagents to form the lipid membrane, a container containing spherical and elliptoid shapes, preferably detergents for extracting the protein of interest and still more preferably reagents to obtain cells expressing the protein of interest. In a preferred embodiment thereof, the kit will contain instructions for preparing the proteoliposomes.

The stabilized proteoliposomes can be used in a variety of different methods.

For example, as a result of the homogeneity of the reconstituted protein, one can use the proteoliposomes for structural characterization of the reconstituted protein.

One can obtain high concentrations of the protein on the bead. In this manner one can use the proteoliposome as an immunogen to obtain antibodies to the native confirmation of the protein. One can use the proteoliposomes to obtain antibodies to different epitopes exposed during different conformations of a protein. For example, one protein may assemble into several different multimeric complexes, depending for example on the availability of different binding partners. Proteoliposomes carrying different complexes can be used as immunogens, thus generating antibodies to different epitopes on a single protein which are differentially exposed depending on its binding to other proteins.

The proteoliposomes can be used to generate and also to identify a range of antibodies. For example, antibodies to gp120 and gp41. For example, antibodies that affect the interaction with the receptor binding sites can be directly screened for, for instance by using a direct binding assay. For example, one can use a radioactive or fluorescent marker to label the gp120 proteoliposome and add soluble CD4, or more preferably a proteoliposome containing CD4. There are various soluble CD4s known in the art including a two-domain (D1D2 sCD4) and a four-domain version. The CD4 proteoliposomes can be added to medium containing the gp120 proteoliposome and an antibody that will block binding between the two proteoliposomes can be screened for. In another example, the proteoliposome can contain both gp120 and CD4 and you can look at interactions with CCR5. Alternatively, when using a derivative from a T cell tropic gp120 one would use a proteoliposome containing CXCR4. Binding can then be directly measured. The antibody of interest can be added before or after the addition of the labeled proteoliposome and the effect of the antibody on binding can be determined by comparing the degree of binding in that situation against a base line standard with that proteoliposome, in the absence of the antibody.

A preferred assay uses the labeled proteoliposome, for example containing a gp120 trimer derived from an M-tropic strain such as JR-FL, iodinated using for instance solid phase lactoperoxidase (in one example having a specific activity of 20 $\mu Ci/\mu g$). The proteoliposome containing the chemokine receptor in this example would contain CCR5. Soluble CD4 could be present.

gp120 Derivatives

The proteoliposome can contain a variety of gp120 derivatives.

In one embodiment, the gp120 trimer is composed of variable region-deleted gp120 or gp125 such as described in U.S. Pat. Nos. 5,858,366 and 5,817,316. For example, the conformational gp120 portion should contain a sufficient number of amino acid residues to define the binding site of the gp120 to the chemokine receptor (e.g. residues 415–425 and the V3 loop) and a sufficient number of amino acids to maintain the conformation of the peptide in a conformation that approximates that of wild-type gp120 bound to soluble CD4 with respect to the chemokine receptor binding site. In other embodiments the V3 loop can be removed to remove masking amino acid residues. In order to maintain the conformation of the polypeptide one can insert linker residues that permit potential turns in the polypeptides structure. For example, amino acid residues such as Gly, Pro and Ala. Gly is preferred. Preferably, the linker residue is as small as necessary to maintain the overall configuration. It should typically be smaller than the number of amino acids in the variable region being deleted. Preferably, the linker is 8 amino acid residues or less, more preferably 7 amino acid residues or less. Even more preferably, the linker sequence is 4 amino acid residues or less. In one preferred embodiment the linker sequence is one residue. Preferably, the linker residue is Gly.

In one preferred embodiment, the gp120 portion also contains a CD4 binding site (e.g. from the C3 region residues 368 and 370, and from the C4 region residues 427 and 457). The chemokine binding site is a discontinuous binding site that includes portions of the C2, C3, C4 and V3 regions. By deletion of non-essential portions of the gp120 polypeptide—such as deletions of portions of non-essential variable regions (e.g. V1/V2) or portions in the constant regions (e.g. C1, C5) one can increase exposure of the CD4 binding site. Another embodiment is directed to a gp120 portion containing a chemokine binding site. Similarly, by deleting the non-essential portions of the protein one can increase exposure of the chemokine binding site. The increased exposure enhances the ability to generate an antibody to the CD4 receptor or chemokine receptor, thereby inhibiting viral entry. Removal of these regions is done while requiring the derivative to retain an overall conformation approximating that of the wild-type protein with respect to the native gp120 binding region, e.g. the chemokine binding region when complexed to CD4. In addition, one can remove glycosylation sites that are disposable for proper folding. Maintaining conformation can be accomplished by using the above-described linker residues that permit potential turns in the structure of the gp120 derivative to maintain the overall three-dimensional structure. Preferred amino acid residues that can be used as linker include Gly and Pro. Other amino acids can also be used as part of the linker, e.g. Ala. Examples on how to prepare such peptides are described more fully in Wyatt, R., et al., *J. Virol.* 69: 5723–5733, 1995; Thali, M., et al., *J. Virol.* 67: 3978–3988, 1993; and U.S. Pat. Nos. 5,858,366 and 5,817,316, which are incorporated herein by reference.

An alternative gp120 derivative is one wherein the linkers used result in a conformation for the derivative so that the discontinuous binding site with the chemokine receptor approximates the conformation of the discontinuous binding site for the chemokine receptor in the wild-type gp120/CD4 complex. These derivatives can readily be made by the person of ordinary skill in the art based upon the above described methodologies and screened in the assays shown herein to ensure that proper binding is obtained.

In one embodiment, at least one sugar addition site is deleted. Preferably the sugar addition site is near a conformational epitope. This can be accomplished by known means. For example, the amino acid can be deleted. In one embodiment that deleted amino acid can be replaced by another residue that will not form a sugar addition site.

In a preferred embodiment, multiple sugar addition sites can be deleted. In a still more preferred embodiment the sugar addition sites can be deleted from the variable loop deleted monomers.

Generating Antibodies

The proteoliposomes can be used to generate an immune reaction in a host by standard means. For example one can administer the proteoliposome in adjuvant.

The proteoliposome is preferably administered with an adjuvant. Adjuvants are well known in the art and include aluminum hydroxide, Ribi adjuvant, etc. Preferably the proteoliposome is comprised of biodegradable material.

One can administer these proteoliposomes to individuals by a variety of means. For example, they can be included in vaginal foams or gels that are used as preventives to avoid infection and applied before people have sexual contact.

The proteoliposomes when used for administration are prepared under aseptic conditions with a pharmaceutically acceptable carrier or diluent.

Doses of the pharmaceutical compositions will vary depending upon the subject and upon the particular route of administration used. Dosages can range from 0.1 to 100,000 µg/kg a day, more preferably 1 to 10,000 µg/kg.

Routes of administration include oral, parenteral, rectal, intravaginal, topical, nasal, ophthalmic, direct injection, etc.

An exemplary pharmaceutical composition is a therapeutically effective amount of an oligomer, antibody etc., that for example affects the ability of the receptor to facilitate HIV infection, or that can induce an immune reaction, thereby acting as a prophylactic immunogen, optionally included in a pharmaceutically-acceptable and compatible carrier. The term "pharmaceutically-acceptable and compatible carrier" as used herein, and described more fully below, includes one or more compatible solid or liquid filler diluents or encapsulating substances that are suitable for administration to a human or other animal. In the present invention, the term "carrier" thus denotes an organic or inorganic ingredient, natural or synthetic, with which the molecules of the invention are combined to facilitate application. The term "therapeutically-effective amount" is that amount of the present pharmaceutical composition which produces a desired result or exerts a desired influence on the particular condition being treated. For example, the amount necessary to raise an immune reaction to provide prophylactic protection. Typically when the composition is being used as a prophylactic immunogen at least one "boost" will be administered at a periodic interval after the initial administration. Various concentrations may be used in preparing compositions incorporating the same ingredient to provide for variations in the age of the patient to be treated, the severity of the condition, the duration of the treatment and the mode of administration.

In one preferred method of immunization one would prime with a proteoliposome containing variable loop deleted gp120 trimer, and then boost with a proteoliposome containing a gp120 trimer that more closely approximates the wild type viral glycoprotein until at least one final boost with proteoliposomes containing the stabilized wild type trimer. For example, if multiple variable regions and sugar addition sites are deleted from the priming trimer, the next boost will be with a trimer where more variable region amino acids are present and/or sugar addition sites present. Each boost will get closer to the wild type configuration until that configuration is reached.

Doses of the pharmaceutical compositions of the invention will vary depending on the subject and upon the particular route of administration used. Dosages can range from 0.1 to 100,000 µg/kg per day, more preferably 1 to 10,000 µg/kg. By way of an example only, an overall dose range of from about, for example, 1 microgram to about 300 micrograms might be used for human use. This dose can be delivered at periodic intervals based upon the composition. For example on at least two separate occasions, preferably spaced apart by about 4 weeks. In the embodiment where the prime is the proteoliposome containing the variable loop deleted gp120 trimers, with the boost of proteoliposomes containing native gp120, or native gp120, it is presently preferred to have a series of at least 2 boosts, preferably 3 to 5 boosts spread out over a year. Other compounds might be administered daily. Pharmaceutical compositions of the present invention can also be administered to a subject according to a variety of other, well-characterized protocols. For example, certain currently accepted immunization regimens can include the following: (i) administration times are a first dose at elected date; a second dose at 1 month after first dose; and a third dose at a subsequent date, e.g., 5 months after second dose. See Product Information, *Physician's Desk Reference,* Merck Sharp & Dohme (1990), at 1442–43. (e.g., Hepatitis B Vaccine-type protocol); (ii) for example with other vaccines the recommended administration for children is first dose at elected date (at age 6 weeks old or older); a second dose at 4–8 weeks after first dose; a third dose at 4–8 weeks after second dose; a fourth dose at 6–12 months after third dose; a fifth dose at age 4–6 years old; and additional boosters every 10 years after last dose. See Product Information, *Physician's Desk Reference,* Merck Sharp & Dohme (1990), at 879 (e.g., Diphtheria, Tetanus and Pertussis-type vaccine protocols). Desired time intervals for delivery of multiple doses of a particular composition can be determined by one of ordinary skill in the art employing no more than routine experimentation.

Antibodies

The term "antibodies" is meant to include monoclonal antibodies, polyclonal antibodies and antibodies prepared by recombinant nucleic acid techniques that are selectively reactive with polypeptides encoded by nucleotide sequences of the present invention. The term "selectively reactive" refers to those antibodies that react with one or more antigenic determinants on e.g. gp120 and do not react with other polypeptides. Antigenic determinants usually consist of chemically active surface groupings of molecules such as amino acids or sugar side chains and have specific three dimensional structural characteristics as well as specific charge characteristics. Antibodies can be used for diagnostic applications or for research purposes, as well as to block binding interactions.

For preparation of antibodies directed toward the immunogenic proteoliposomes, any technique that provides for the production of antibody molecules may be used.

For example, mice can be immunized twice intraperitoneally with approximately 50 micrograms of proteoliposome immunogen per mouse. Sera from such immunized mice can be tested for antibody activity by immunohistology or immunocytology on any host system expressing such polypeptide or against another proteoliposome or by ELISA with the expressed polypeptide. For immunohistology, active antibodies of the present invention can be identified using a biotin-conjugated anti-mouse immunoglobulin followed by avidin-peroxidase and a chromogenic peroxidase substrate. Preparations of such reagents are commercially available; for example, from Zymed Corp., San Francisco, Calif. Mice whose sera contain detectable active antibodies according to the invention can be sacrificed three days later and their spleens removed for fusion and hybridoma production. Positive supernatants of such hybridomas can be identified using the assays described above and by, for example, Western blot analysis.

Another method for preparing antibodies is by using hybridoma mRNA or splenic mRNA as a template for PCT amplification of such genes [Huse, et al., *Science* 246:1276 (1989)]. For example, intrabodies can be derived from murine monoclonal hybridomas [Richardson, J. H., et al., *Biochem and Biophys Res Comm.* 197: 422–427 (1993); Mhashilkar, A. M., et al., *EMBO J.* 14:1542–1551 (1995)]. These hybridomas provide a reliable source of well-characterized reagents for the construction of antibodies and are particularly useful when their epitope reactivity and affinity has been previously characterized. Another source for such construction includes the use of human monoclonal antibody producing cell lines [Marasco, W. A., et al., *Proc. Natl. Acad. Sci. USA* 90:7889–7893 (1993); Chen, S. Y., et al., *Proc. Natl. Acad. Sci. USA* 91:5932–5936 (1994)]. Another example includes the use of antibody phage display technology to construct new antibodies against different epitopes on a target molecule [Burton, D. R., et al., *Proc. Natl. Acad. Sci. USA* 88:10134-1-137 (1991); Hoogenboom, H. R., et al., *Immunol. Rev.* 130:41–68 (1992); Winter, G., et al., *Ann. Rec. Immunol.* 12:433–355 (1994); Marks, J. D., et al., *J Biol. Chem.* 267:16007–16010 (1992); Nissim, A., et al., *EMBO J.* 13:692–698 (1994); Vaughan, T. J., et al., *Nature Bio.* 14:309–314 (1996); Marks, C., et al., *New Eng. J. Med.* 335: 730–733 (1996)]. For example, very large naive human sFV libraries have been and can be created to offer a large source of rearranged antibody genes against a plethora of target molecules. Smaller libraries can be constructed from individuals with autoimmune disorders [Portolano, S,. et al., *J. Immunol.* 151:2839–2851 (1993); Barbas, S. M., et al., *Proc. Natl. Acad. Sci. USA* 92:2529–2533 (1995)] or infectious diseases [Barbas, C. F., et al., *Proc. Natl. Acad. Sci. USA* 89:9339–9343 (1992); Zebedee, S. L., et al., *Proc. Natl. Acad. Sci. USA* 89:3175–3179 (1992)] in order to isolate disease specific antibodies.

Other sources include transgenic mice that contain a human immunoglobulin locus instead of the corresponding mouse locus as well as stable hybridomas that secrete human antigen-specific antibodies [Lonberg, N., et al., *Nature* 368:856–859 (1994); Green, L. L., et al., *Nat. Genet.* 7:13–21 (1994)]. Such transgenic animals provide another source of human antibody genes through either conventional hybridoma technology or in combination with phage display technology. In vitro procedures to manipulate the affinity and find specificity of the antigen binding site have been reported including repertoire cloning [Clackson, T., et al., *Nature* 352: 624–628); marks, J. D., et al., *J. Mol. Biol.* 222: 581–597 (1991); Griffiths, A. D., et al., *EMBO J.* 12: 725–734 (1993)], in vitro affinity maturation [Marks, J. D., et al., *Biotech* 10: 779–783 (1992); Gram, H., et al., *Proc. Natl. Acad. Sci. USA* 89: 3576–3580 (1992)], semi-synthetic libraries [Hoogenboom, H. R., supra; Barbas, C. F., supra; Akamatsu, Y., et al., *J. Immunol.* 151: 4631–4659 (1993)] and guided selection [Jespers, L. S. et al., *Bio Tech* 12: 899–902 (1994)]. Starting materials for these recombinant DNA based strategies include RNA from mouse spleens [Clackson, t., supra] and human peripheral blood lymphocytes [Portolano, S., et al., supra; Barbas, C. F., et al., supra; Marks, J. D., et al., supra; Barbas, C. F., et al., *Proc. Natl. Acad. Sci. USA* 88: 7978–7982 (1991)] and lymphoid organs and bone marrow from HIV-1-infected donors [Burton, D. R., et al., supra; Barbas, C. F., et al., *Proc. Natl. Acad. Sci. USA* 89:9339–9343 (1992)].

For preparation of monoclonal antibodies directed toward the proteoliposomes, any technique that provides for the production of antibody molecules by continuous cell lines may be used. For example, the hybridoma technique originally developed by Kohler and Milstein (*Nature,* 256: 495–7, 1973), as well as the trioma technique, the human B-cell hybridoma technique (Kozbor et al., *Immunology Today* 4:72), and the EBV-hybridoma technique to produce human monoclonal antibodies, and the like, are within the scope of the present invention. See, generally Larrick et al., U.S. Pat. No. 5,001,065 and references cited therein. Further, single-chain antibody (SCA) methods are also available to produce antibodies against polypeptides encoded by a eukaryotic nucleotide sequence of the invention (Ladner et al., U.S. Pat. Nos. 4,704,694 and 4,976,778).

The monoclonal antibodies may be human monoclonal antibodies or chimeric human-mouse (or other species) monoclonal antibodies. The present invention provides for antibody molecules as well as fragments of such antibody molecules.

Those of ordinary skill in the art will recognize that a large variety of possible moieties can be coupled to the resultant antibodies or preferably to the stabilized trimers or to other molecules of the invention. See, for example, "Conjugate Vaccines", *Contributions to Microbiology and Immunology*, J. M. Cruse and R. E. Lewis, Jr (eds.), Carger Press, New York, 1989, the entire contents of which are incorporated herein by reference.

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, disocyanates, glutaraldehydes, diazobenzenes and hexamethylene diamines. This listing is not intended to be exhaustive of the various classes of coupling agents known in the art but, rather, is exemplary of the more common coupling agents (see Killen and Lindstrom, *J. Immunol.* 133:1335–2549, 1984; Jansen, F. K., et al., *Imm. Rev.* 62:185–216, 1982; and Vitetta et al., supra).

Preferred linkers are described in the literature. See, for example, Ramakrishnan, S., et al., *Cancer Res.* 44: 201–208 (1984), describing the use of MBS (M-maleimidobenzoyl-N-hydroxysuccinimide ester). See also Umemoto et al., U.S. Pat. No. 5,030,719, describing the use of a halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pyridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide]hexanoate (Pierce Chem. Co. Cat. #2165-G); and (v) sulfo-NHS (N-hydroxysulfosuccinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

Complexes that form with molecules of the present invention can be detected by appropriate assays, such as the direct binding assay discussed earlier and by other conventional types of immunoassays.

In a preferred embodiment, one could screen a phage display library looking to find antibodies to a given protein or find ligands that will bind to the protein.

One can also use these proteoliposomes to screen libraries for a desired compound. One can also use these proteoliposomes to screen complex chemical libraries of small molecular weight (<1000 daltons) compounds to identify high-affinity ligands. These compounds could serve as lead compounds for the discovery of agonistic and antagonistic drugs.

If one knows a ligand that interacts with the protein, one can use these proteoliposomes in assays to screen for compounds that modulate such interactions with the protein. For example, in the aforementioned CCR5/CD4-containing proteoliposomes, one can add gp120 to the mixture and add other compounds to see their effect on the formation or stability of the CD4/gp120/CCR5 complex.

One can also use the antibody tag to reverse-orient the proteoliposome. As used herein a reverse-oriented protein will have the portion of the protein that is normally present intracellularly present on the surface of the proteoliposome. Then one can screen for compounds or proteins that effect intracellular interactions. For example, one can look at the binding of intracellular as well as extracellular ligands, as well as compounds or proteins that will affect intracellular as well as extracellular binding.

The present method is not limited to multiple membrane spanning proteins that bind small ligands. Virtually any integral membrane protein can be studied.

One can also use this method to identify small antagonists in an assay that looks at compounds that affect binding of a known ligand. For instance, the entry of human immunodeficiency virus (HIV-1) into host cells typically requires the sequential interaction of the gp120 exterior envelope glycoprotein with the CD4 glycoprotein and a chemokine receptor on the cell membrane. CD4 binding induces conformational changes in gp120 that allow high-affinity binding to the chemokine receptor. The β-chemokine receptor CCR5 is the principal HIV-1 coreceptor used during natural infection and transmission. Individuals with homozygous defects in CCR5 are healthy but relatively resistant to HIV-1 infection. Although some HIV-1 isolates can be adapted in tissue culture to replicate on cells lacking CD4, binding to the chemokine receptor appears to be essential for virus entry into the host cell. These observations suggest that inhibiting the gp120-CCR5 interaction might be a useful therapeutic or prophylactic approach to HIV-1 infection. A chemokine analogue, AOP-RANTES (Simmons, G. et al. (1997), *Science:* 276: 276–279), and a small molecular weight compound (TaKeda) (Baba, M. et al. (1999), *Proc. Natl. Acad. Sci. USA* 96: 5698–5703) have been identified that bind CCR5 and inhibit HIV-1 infection in tissue culture, although clinical utility remains to be demonstrated.

When solubilized using specific detergent and salt conditions, human CCR5 can retain its ability to bind HIV-1 gp120-CD4 complexes and conformation-dependent monoclonal antibodies (Mirzabekov et al., JBC). However, the detergent-solubilized CCR5 exhibits very stringent requirements with respect to the conditions under which native conformation is retained and has limited longevity. Thus, it is impractical to use purified preparations of solubilized CCR5 in screening assays. CCR5-proteoliposomes have homogeneous, native CCR5 affixed to the surface of a paramagnetic bead in an oriented manner. The preparation of CCR5-proteoliposomes is relatively independent of the CCR5 density on the surface of the cells used as a source of the chemokine receptor, and also allows the concentration of CCR5 on the bead surface. A lipid bilayer, such as that reconstituted around the bead, provides a natural membrane environment for the CCR5 protein, allowing long-term maintenance of the native CCR5 conformation.

Accordingly, the present method creates an easily manipulable spherical lipid bilayer containing a relatively large amount of pure, oriented and stable integral membrane protein. This permits these proteins to be used in applications that have previously been restricted to the use of soluble purified proteins.

As a specific example, paramagnetic, nonporous beads surrounded by a lipid membrane bilayer containing human CCR5 in a native conformation can be prepared as set forth below. Human CCR5 can be expressed in Cf2Th canine thymocytes transfected with a codon-optimized CCR5 gene. The CCR5 protein contains a C-terminal nonapeptide (C9) tag that is recognized by the 1D4 monoclonal antibody. In a first approach, lysates from CCR5-expressing Cf2Th cells (Cf2Th-CCR5) were prepared using the detergents shown to allow retention of native CCR5 formation. CCR5 was affinity-purified from the lysates using 1D4-Sepharose beads and eluted using the C9 nonapeptide corresponding to the C-terminal epitope tag. The CCR5 in detergent solution was added, along with a detergent-solubilized lipid mixture containing 1% biotin-DPPE, to streptavidin-coated beads. During subsequent removal of the detergent by dialysis, CCR5 molecules were incorporated into the lipid membrane that self-assembled around the bead. FACS analysis of these beads revealed equivalent recognition of CCR5 by two antibodies, the 5C7 antibody directed against a linear N-terminal CCR5 epitope and the 1D4 antibody against the C-terminal epitope tag (data not shown). As the 5C7 and 1D4 epitopes are expected to reside on opposite sides of the membrane in native CCR5, this result suggests a random (50% inside-in, 50% inside-out) orientation of CCR5 in the lipid membrane. To examine the conformational status of the CCR5 in the membrane, recognition by the 5C7 antibody was compared with that by the 2D7 antibody, which recognizes a conformation-dependent epitope in the CCR5 ectodomain. Recognition of the reconstituted CCR5 by 2D7 was lower than that by 5C7 (data not shown), indicating that only a fraction of the CCR5 retained a native conformation.

In a second approach, detergent-solubilized CCR5 was captured onto paramagnetic beads conjugated with the 1D4 antibody. Following the addition of detergent-solubilized lipids and dialysis, the membrane was reconstituted based solely on the attraction of lipid molecules to the hydrophobic membrane-spanning regions of CCR5. FACS and confocal microscopic analysis of these proteoliposomes was performed using the 5C7 and 2D7 antibodies conjugated with phycoerythrin. In some experiments, the lipid membrane bilayer was visualized by preparing the proteoliposomes with rhodamine-conjugated DOPE. These results indicated that the beads acquired membrane with much lower efficiency than in the method described above. Moreover, a fraction of CCR5 appeared to be denatured (data not shown).

In a third approach, the method of the present invention was used (FIG. 1). Paramagnetic beads were conjugated with both the 1D4 antibody and the streptavidin. The 1D4 antibody allowed simple purification and concentration of CCR5 from cell lysates, as well as its orientation on the bead surface. The streptavidin allowed stable and saturating membrane reconstitution around the bead. A 10:1 molar ratio of 1D4 antibody:streptavidin was found to be optimal with respect to the highest density of reconstituted CCR5 and the completeness of the membrane in the paramagnetic proteoliposomes (data not shown). It is possible to vary the antibody:streptavidin ratio, if necessary, from 100:1 to 1:1000 or less in different applications.

Of the three approaches employed, CCR5-proteoliposomes prepared by the third approach exhibited the most efficient recognition by the 2D7 conformation-dependent antibody. In fact, recognition by the 2D7 antibody was practically equal to that of the 5C7 antibody (data not shown), indicating that the vast majority of CCR5 in these proteoliposomes preparations is in a native conformation.

The properties of and the methods in which these proteoliposomes can be used are discussed below:

a) Purity of the reconstituted protein. The method for the production of the proteoliposome, e.g., CCR5-proteoliposomes, allows purification of the protein prior to reconstitution into lipid membranes. This feature permitted us to examine ligand binding such as HIV-1 gp120 binding to essentially pure CCR5 in the proteoliposomal membrane. In this instance, no other cellular protein appeared to be required in stoichiometric amounts for the efficient binding of gp120 to CCR5, other than the sCD4 glycoprotein. Accordingly, one can use this proteoliposome technology to address whether cellular proteins (e.g., proteins other than CD4 and CCR5) are necessary for membrane fusion mediated by the HIV-1 envelope glycoproteins.

The purity of the reconstituted protein is advantageous for the use of the paramagnetic proteoliposomes to identify ligands from libraries of recombinant proteins or chemical compounds. For example, we have recently selected antibodies directed against CCR5 by using the paramagnetic CCR5-proteoliposomes to screen a phage display library of single-chain antibody fragments (Kontos et al., unpublished data). Similarly, screening of chemical compound libraries is possible by incubation of paramagnetic proteoliposomes with complex mixtures, followed by removal and analysis of the moieties that interact with the reconstituted membrane protein of interest. In another format, paramagnetic proteoliposomes containing the target membrane protein of interest and fluorescently labeled can be used to detect ligands among a large array of chemical compounds anchored on solid support.

The presence of pure protein antigen in the paramagnetic proteoliposomes will promote the generation of more specific immune responses in animals immunized with these preparations.

The purity of the reconstituted membrane protein in the proteoliposomes may be a disadvantage for some applications. For example, if the binding of a ligand of interest is dependent upon other cellular moieties, studies with proteoliposomes may imperfectly mimic the binding events that transpire at the surface of a cell. For example, we have been unable to demonstrate efficient binding of the β-chemokine, MIP-1α, to our CCR5-proteoliposomes (data not shown), indicating that the requirements for the binding of HIV-1 gp120 and MIP-1 α to CCR5 may differ. It has been suggested that the efficient binding of some chemokines to their receptors is dependent upon proteoglycans on the cell surface or upon dimerization or G protein coupling of the receptor (Zeng, F. Y. et al (1999), *J. Biol. Chem.* 274:19487–19497). However, one can create CCR5 proteoliposomes containing these additional factors to confirm their role in ligand binding.

b) Homogeneity of the reconstituted protein. Our preferred protocol utilizes beads conjugated with both streptavidin and an antibody such as the 1D4 antibody against the C-terminal epitope tag on CCR5. The inclusion of streptavidin allows the fixation of biotinylated lipid to the bead surface and results in a more stable and complete membrane surrounding the bead. For example, the CCR5 reconstituted into these membranes exhibited more conformational homogeneity based on relative recognition by the 5C7 and 2D7 antibodies. The homogeneity of the reconstituted protein in the proteoliposomes can be important for structural characterization of the reconstituted protein.

c) Concentration of the reconstituted protein. The concentration of the reconstituted protein in the proteoliposomes is determined by the density of the conjugated capture antibody on the bead surface and the concentration of the protein of interest in the cell lysates. These two parameters can be manipulated by known means to allow adequate concentration of proteins of interest that are expressed at only modest levels in the producing cells.

d) Orientation of the reconstituted protein. The conjugation to the beads of particular antibodies that recognize the extracellular or intracytoplasmic portions of the reconstituted protein of interest allow its orientation in the proteoliposome membrane. For instance, in addition to the use of the 1D4 antibody against the CCR5 C-terminal epitope tag to orient CCR5, you can also conjugate the 2D7 antibody to the bead surface, allowing an inside-out (reverse) orientation of CCR5 in the proteoliposome (data not shown). The capability of achieving either orientation of the protein in the paramagnetic proteoliposomes allows the binding of intracellular as well as extracellular ligands to be studied.

The paramagnetic proteoliposomes are stable for extended periods of time. The integrity of the conformation-dependent CCR5 epitope recognized by the 2D7 antibody was preserved after exposure of the CCR5-proteoliposomes to harsh conditions (high or low pH, extremes of ionic strength, ranges of temperature). Because several of these conditions have been shown to denature detergent-solubilized CCR5 (Mirzabekov), the observed conformational stability indicates that CCR5 in the proteoliposomes is in an environment, presumably within the lipid membrane, that is strongly conducive to the preservation of native structure. This property allows the rapid exchange of external buffers that is useful for functional studies of several types of integral membrane proteins. The long-term storage of the proteoliposomes is also facilitated by the stability of the native conformation of the protein of interest in this context.

EXAMPLES

Example 1

Proteoliposomes Containing CCR5
Construction and Expression of Codon-optimized CCR5 (synCCR5)

The analysis of codon usage for 45 GPCRs representing different protein subfamilies was performed with GenBank™ data and software developed by the University of Wisconsin Genome Sequence Group. The sequence encoding human CCR5 was optimized for mammalian cell codon usage (Andre, S., et al. (1999). *J. Virology* 72: 1497–1503) utilizing the following codons: alanine (GCC), arginine (CGC), asparagine (AAC), aspartic acid (GAC), cysteine (TGC), glutamic acid (GAG), glutamine (CAG), glycine (GGC), histidine (CAC), isoleucine (ATC), leucine (CTG), lysine (AAG), methionine (ATG), phenylalanine (TTC), proline (CCC), serine (TCC), threonine (ACC), tryptophan (TGG), tyrosine (TAC), and valine (GTG). The 5' and 3' sequences flanking the CCR5 coding sequence were modified. Following restriction sites for EcoRV, EcoRI and HindIII, the Kozak consensus (GCCGCCACC<u>ATGG</u>) (SEQ ID NO:1) was placed immediately 5' to the CCR5 reading frame. A sequence encoding a single glycine residue followed by the bovine rhodopsin C9 peptide tag (TETSQVAPA) (SEQ ID NO:2) was introduced immediately 5' to the natural stop codon of CCR5. At the 3' end of the epitope-tagged CCR5 gene, XbaI, SalI, and NotI restriction sites were introduced. Analogous constructs were made for the wild-type human CCR5 gene and the bovine rhodopsin gene, except that the codons were not altered and, in the latter case, the C-terminal C9 sequence was naturally present.

A total of 34 oligonucleotides, each approximately 70 nucleotides in length, corresponding to the complete sense and antisense strands of the synCCR5 gene and flanking sequences, were constructed so that approximately 50% of their sequences were complementary to those of each of the two complementary oligonucleotides from the opposite strand. Oligonucleotides were deprotected in pure ammonium hydroxide at 65° C. for 4 h, after which the ammonium hydroxide was evaporated, and the oligonucleotides were dissolved in water at a final concentration of 2 nM. For gene synthesis, the 34 oligonucleotides were separated into five groups (6 or 8 oligonucleotides per group) and 25 cycles of polymerase chain reaction were performed using Pfu polymerase (Stratagene, La Jolla, Calif.) and a 3-fold molar excess of the 5' and 3' terminal oligonucleotides in each group. This step generated five small segments of the synCCR5 gene with complementary and overlapping ends. Equal amounts of each polymerase chain reaction product were combined with a 3-fold molar excess of the 5' and 3' terminal oligonucleotides of the complete synCCR5 sequence. A second round of 25 cycles of polymerase chain reaction yielded the complete synCCR5 sequence. The product was sequenced to ensure that the sequence was correct.

The synCCR5, wild-type CCR5, and bovine rhodopsin sequences were cloned into the following vectors: PMT4 (a gift from Dr. Reeves, Massachusetts Institute of Technology), PACH (a gift from Dr. Velan, Israel Institute for Biological Research), pcDNA 3.1(+) and pcDNA4/HisMax (Invitrogen), and PND (a gift from Dr. Rhodes, University of California, Davis). After cloning of the synCCR5 gene into the pcDNA4/HisMax vector, the sequence encoding the N-terminal HisMax region was removed by QuikChange mutagenesis (Stratagene). Different cell lines were transfected with the synCCR5 and wild-type CCR5 genes using the GenePorter transfection reagent (San Diego, Calif.). Following transfection, cells expressing CCR5 were selected with 0.8 mg/ml of neomycin (G418). Cells expressing the highest surface levels of CCR5 were selected by FACS after staining cells with the R-phycoerythrin-conjugated anti-CCR5 antibody 2D7-PE (Pharmingen, San Diego, Calif.). Among all tested cells (canine thymocytes Cf2Th, human embryonic kidney cells HEK-293T, COS-1, and HeLa (American Type Culture Collection)), the highest CCR5 expression levels were observed in Cf2Th and HEK-293T cells transfected with synCCR5 gene in the PACH vector. The highest synCCR5-expressing clones were selected by FACS from a total of 76 clones of Cf2Th cells and 62 clones of HEK-293T cells.

Radiolabeling and Immunoprecipitation of CCR5

Approximately $4 \times 10^6$ CCR5-expressing Cf2Th or HEK-293T cells grown to full confluency in 100-mm dishes were washed twice in PBS and starved for 1 h at 37° C. in Dulbecco's modified Eagle's medium without cysteine and methionine (Sigma) or in sulfate-free media (ICN, Costa Mesa, Calif.). The starvation medium was removed and 200 µCi each of [$^{35}$S]methionine and [$^{35}$S]cysteine or 500 µCi of [$^{35}$S]sulfate (NEN Life Science Products) in 4 ml of medium was added to the cells for various times for pulse-chase experiments or overnight (12 h) in all other cases. Cells were washed twice with PBS and lysed in 1 ml of solubilization medium composed of 100 mM $(NH_4)_2 SO_4$, 20 mm Tris-HCl (pH 7.5), 10% glycerol, 1% (w/v) detergent (see below), and Protease Inhibitor Mixture (one tablet of Complete™ (Roche Molecular Biochemicals) per 25 ml). The lysate was incubated at 4° C. for 30 min on a rocking platform, and cell debris was removed by centrifugation at 14,000×g for 30 min. CCR5 was precipitated with 20 µl of 1D4-Sepharose beads (Reeves, P., Thurmond, R. L., and Khorana, G. G. (1996) *Proc. Natl. Acad. Sci. USA* 4: 7784–90) overnight, after which the beads were washed six times in the solubilization medium and pelleted. An equal volume of 2× SDS-sample buffer was added to the beads, followed by resuspension and incubation for 1 h at 55° C. Samples were run on 11% SDS-polyacrylamide minigels, which were visualized by autoradiography or analyzed on a Molecular Dynamics PhosphorImager SI (Sunnyvale, Calif.).

A total of 18 detergents were tested in the solubilization buffers. The detergents, with abbreviations and critical micelle concentrations in parentheses, were n-octyl-β-D-glucopyranoside (23.4 mM), n-decyl-β-D-maltoside (1.8 mM), n-dodecyl-β-D-maltoside (DDM) (0.17 mM), cyclohexyl-butyl-β-D-maltoside (Cymal™-4, 7.6 mM), cyclohexyl-pentyl-β-D-maltoside (Cymal™-5, 2.4 mM), cyclohexyl-hexyl-β-D-maltoside (Cymal™-6, 0.56 mM), cyclohexyl-heptyl-β-D-maltoside (Cymal™-7, 0.19 mM), cyclo-hexylpropanoyl-N-hydroxyethylglucamide (108 mM), cyclohexylbutanoyl-N-hydroxyethylglucamide (35 mM), cyclohexylpentanoyl-N-hydroxyethyglucamide (11.5 mM), N-octylphosphocholine (Fos-Choline™ 8, 114 mM), N-decylphosphocholine (Fos-Choline™ 10, 11 mM), N-dodecylphosphocholine (Fos-Choline™ 12, 1.5 mM), N-tetradecylphosphocholine (Fos-Choline™ 14, 0.12 mM), Triton X-100 (0.02 mM), CHAPS (8 mM), Nonidet P-40 (0.02 mM), and diheptanoyl-phosphocholine (DHPC) (1.4 mm). All detergents were purchased from Anatrace (Maumee, Ohio) except DHPC, which was purchased from Avanti Polar Lipids (Alabaster, Ala.).

Purification of CCR5

Stable Cf2Th/PACH/synCCR5 cells grown to full confluency in a 150-mm dish were incubated with medium containing 4 mM sodium butyrate for 40 h, washed in PBS, detached by treatment with 5 mM EDTA/PBS, pelleted, and again washed in PBS. Cells were solubilized for 30 min with 3 ml of the solubilization medium containing Cymal™-5 and centrifuged for 30 min at 14,000×g. The cell lysate was incubated with 50 µl of 1D4-Sepharose beads on a rocking platform at 4° C. for 10–12 h. The Sepharose beads were washed five times with the washing buffer (100 mM $(NH_4)_2SO_4$, 20 mM Tris-HCl (pH 7.5), 10% glycerol, and 1% Cymal™-5) and once with washing buffer plus 500 mM $MgCl_2$. CCR5 was eluted from the beads by three successive washes with 50 µl of medium containing 200 µM C9 peptide (SEQ ID NO:2) (TETSQVAPA), 500 mM $MgCl_2$ 100 mM $NH_4)_2SO_4$, 20 mM Tris-HCl (pH 7.5), 10% glycerol, and 0.5% Cymal™-5. The total quantity of harvested CCR5 was estimated by Coomassie Blue staining of an SDS-polyacrylamide gel run with standard quantities of bovine serum albumin.

Binding of HIV-1 gp120 Envelope Glycoproteins to Solubilized CCR5

Approximately $4 \times 10^6$ Cf2Th/PACH/synCCR5 cells were labeled for 12 h with [$^{35}$S]Met/Cys and lysed in solubilization buffer containing 1% Cymal™-5. One ml of cleared cell lysate was incubated with 100–500 µl of the gp120-containing solutions. The unlabeled JR-FL gp120 was produced in Drosophila cells (Wu, L., et al. (1996), *Nature* 384, 179–183), and the ADA and 190/197 R/S gp120 glycoproteins were produced from transiently transfected 293T cells that had been radiolabeled with [$^{35}$S]Met/Cys overnight. Except in the case of the CD4-independent gp120 variant, 190/197 R/S, the gp120 glycoproteins (2–4 µg) were preincubated with sCD4 (2–4 µg) in 20 ml of PBS for 1 h at 22° C. prior to addition to the CCR5-containing lysates. After 12 h at 4° C., the gp120-CCR5 complexes were precipitated with either the C11 anti-gp120 antibody (kindly provided by Dr. James Robinson, Tulane University Medical School) or with the 1D4 antibody.

Expression of CCR5 in Mammalian Cells

We compared the codon usage for opsins, the only GPCRs that are naturally highly expressed, with the codon usage for 45 other GPCRs representing a spectrum of different GPCR subfamilies. Opsin codons are biased toward those shown to be optimal for efficient translation in mammalian cells (Andre, S., et al (1998), *J. Virol.* 72: 1497–1503), whereas other GPCRs, including CCR5, are associated with codons that are more random and, in many cases, inefficiently translated (data not shown). A codon-optimized CCR5 gene was designed, synthesized using the polymerase chain reaction, and transiently expressed in several different cell lines, using five different expression vectors (pcDNA 3. 1, PACH, PND, PMT4, and pcDNA4/HisMax). The level of CCR5 expression directed by the codon-optimized gene was 2–5 times that directed by the wild-type CCR5 gene. Among the cell lines tested, CCR5 expression was the highest in Cf2Th canine thymocytes (data not shown), so these cells were used to generate stable cell lines. The PACH vector was used to express the codon-optimized gene encoding human CCR5 containing a 9-residue C-terminal epitope tag (the C9 tag) derived from bovine rhodopsin. The presence of the C9 tag allows recognition of the CCR5 protein by the 1D4 antibody (Oprian, D. D., et al. (1987), *Proc. Natl. Acad. Sci. USA.* 84: 8874–8878). CCR5 expression in the stable cell line, designated Cf2Th/PACH/synCCR5, could be enhanced 2–3 fold by treatment of the cells with sodium butyrate. Following this treatment, approximately 3–5 µg of CCR5 of high purity could be isolated from $10^7$ Cf2Th/PACH/synCCR5 cells, using techniques described below.

Precursor and Mature Forms of CCR5

CCR5 synthesis and turnover in Cf2Th cells were studied by pulse-chase analysis. A precursor of approximately 40 kDa chased into the mature form of CCR5, which migrated as a wide band of approximately 43 kDa. The CCR5 precursor exhibited a half-life of approximately 25 min. The half-life of the mature form of CCR5 was 11–14 h, regardless of whether CCR5 expression was directed by the wild-type or codon-optimized CCR5 gene. The half-lives of the precursor and mature forms of CCR5 in HEK-293 cells were similar to those in Cf2Th cells (data not shown). In several different cell lines, a lower molecular mass (approximately 36 kDa) form of CCR5 appeared in parallel with the mature protein. This lower molecular mass form of CCR5 was expressed at lower levels than the mature form of CCR5 and has not been completely characterized. Its identity as a CCR5 isoform was confirmed by its precipitation by the 1D4 antibody and the anti-CCR5 antibody 2D7 and by mass spectrometry (FIG. 2 and data not shown).

Solubilization of Native CCR5

Figure 2A:
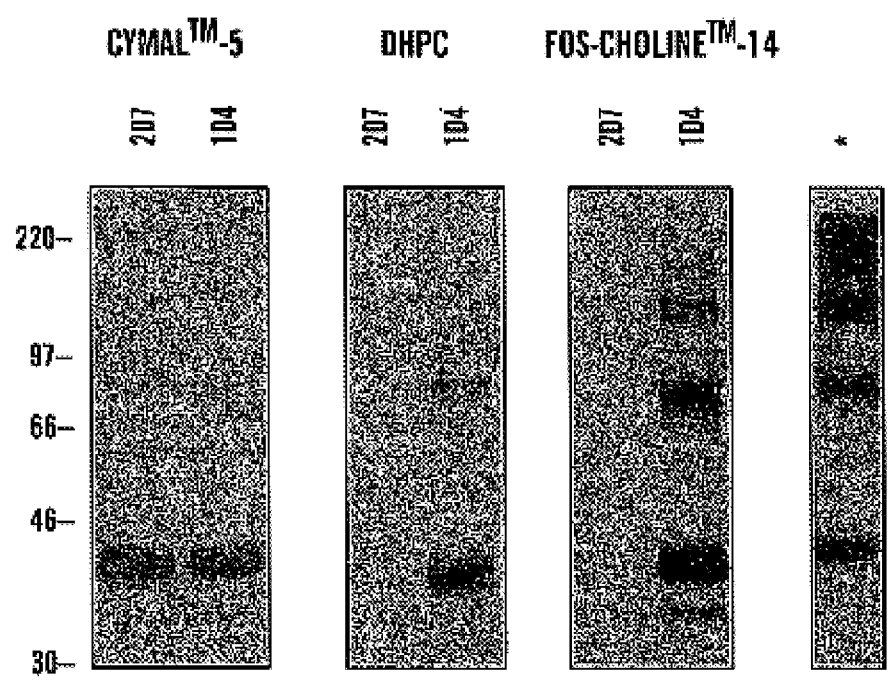
FIGS. 2A and 2B show maintenance of native CCR5 conformation in buffers containing different detergents. Approximately 4×10$^6$ [$^{35}$S]Met/Cys-labeled Cf2Th/PACH/synCCR5 cells were lysed in 1 ml of ice-cold solubilization buffer (100 mM $(NH_4)_2SO_4$, 20 mM Tris-HCl (ph 7.5), 10% glycerol) supplemented with a protease inhibitor mixture and 1% (w/v) of different detergents. After 30 min of solubilization and 30 min of centrifugation, the cleared cell lysates were separated into two equal portions. One portion was precipitated with 2D7 (a conformation-dependent antibody against CCR5) and the other portion with 1D4 (an antibody that recognizes the linear C9 epitope tag). The precipitates were run on SDS-polyacrylamide gels, and two parameters were examined: 1) the total quantity of CCR5 precipitated by the 1D4 antibody, and 2) the ratio of CCR5 precipitated by the 2D7 antibody relative to that precipitated by the 1D4 antibody.
Figure 2B:
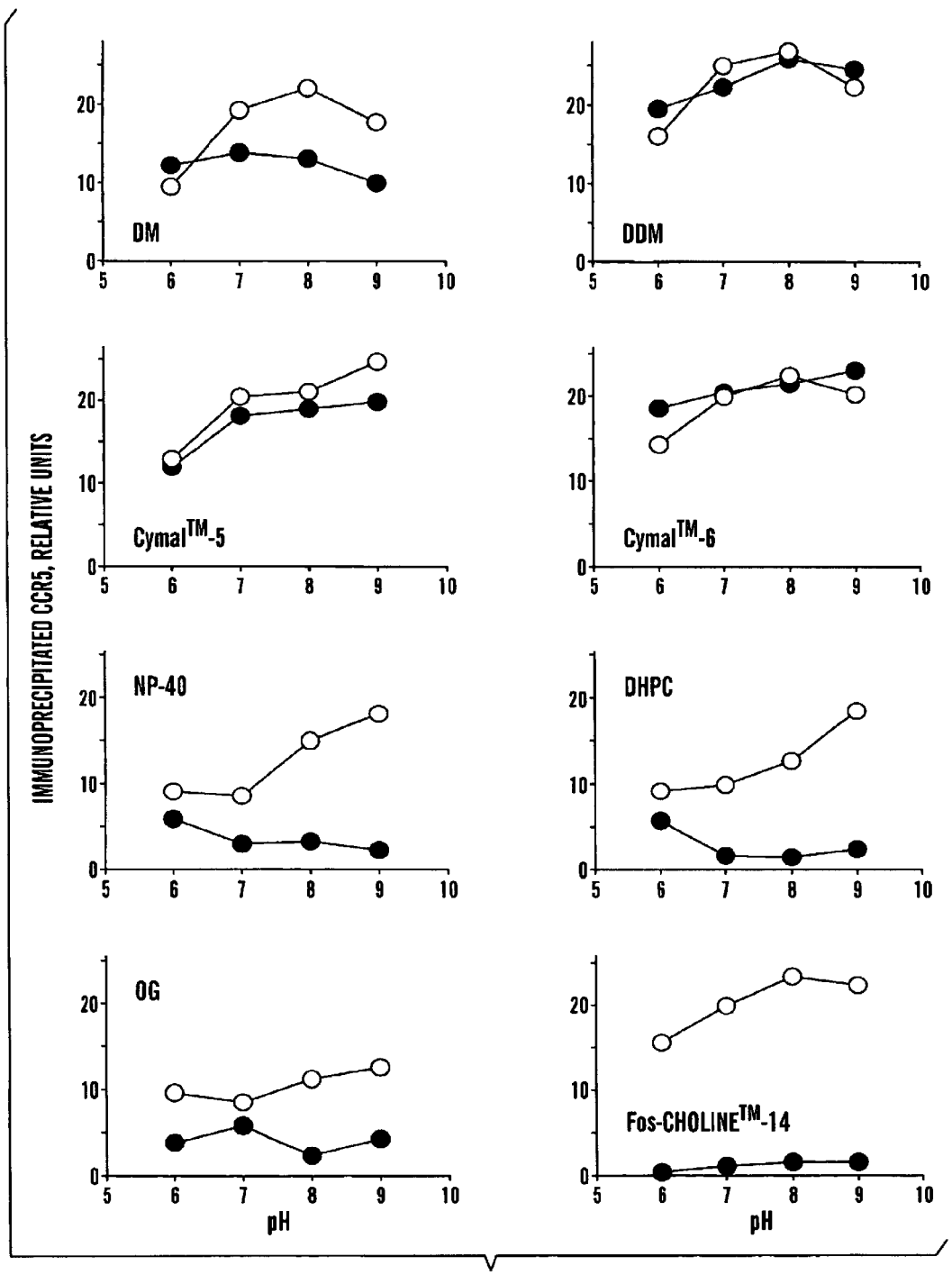

Membrane protein purification requires solubilization of the membranes, typically through the use of detergents. A broad spectrum of conditions was studied to arrive at the composition of the buffer that allowed solubilization and isolation of native CCR5. This optimization was guided by a comparison of the amount of solubilized CCR5 capable of being precipitated by the 2D7 antibody, which recognizes a conformation-dependent CCR5 epitope (Wu, L., et al. (1997), *J. Exp. Med.* 186: 1373–1381), with that able to be precipitated by the 1D4 antibody directed against the linear C9 epitope tag. In this manner, the percentage of solubilized CCR5 remaining in a native conformation could be estimated (FIG. 2A). Eighteen detergents, most of which were designed specifically for the extraction and purification of membrane proteins, were studied. In terms of the quantity of isolated CCR5 protein, as well as the percentage of protein in a conformation able to be recognized by the 2D7 antibody, the most effective detergents were DDM, Cymal™-5, and Cymal™-6 (FIG. 2B). Of these detergents, Cymal™-5 exhibits the highest critical micelle concentration (2.4 mM), facilitating dialysis of the detergent from the protein solution for the purposes of membrane reconstitution and/or crystallization. We also found that a CCR5 conformation competent for binding HIV-1 gp120 was best preserved in buffers containing Cymal™-5 (see below). Therefore, Cymal™-5 was used for further refinement of the CCR5 solubilization/isolation protocol, examining a number of variables (salt composition and concentration, pH, temperature, and minor additives) known to influence the stability of solubilized proteins (Hamaguchi, K. (1992) *The Protein Molecule. Conformation, Stability and Folding*, Japan Scientific Societies Press, Springer-Verlag, New York). Ammonium sulfate and glycerol were found to prolong the existence of a CCR5 conformation capable of being recognized by the 2D7 antibody (data not shown). The optimized CCR5 solubilization buffer was composed of 100 mM $(NH_4)_2SO_4$, 20 mM Tris-HCl (pH 7.5), 10% glycerol, and 1% Cymal™-5.

CCR5-expressing Cells

The cell line (Cf2Th/CCR5) stably expressing approximately $10^6$ molecules of CCR5 per cell was generated by transfection of Cf2Th canine thymocytes with the above-described codon-optimized CCR5 gene. The C-terminus of the expressed CCR5 consists of a glycine residue followed by the C9 nonapeptide TETSQVAPA (SEQ ID NO: 2), which contains the epitope for the 1D4 antibody. Wild-type and C-terminally tagged CCR5 molecules have been shown to be functionally comparable. Cf2Th/CCR5 cells grown to full confluency in 150 mm dishes were harvested using 5 mM EDTA in PBS, washed in PBS, pelleted and frozen until needed.

Radiolabeling of Cells Expressing CCR5 or gp120

Cf2Th/CCR5 cells were radiolabeled in 150 mm dishes for 12 hours with 10 ml/dish of Met-Cys-free DMEM supplemented with 400 µCi each of $^{35}$S-methionine and $^{35}$S-cysteine (NEN Life Science Products, Boston, Mass.). Labeled cells were harvested using 5 mM EDTA in PBS, pelleted and frozen until needed.

To label the HIV-1 gp120 envelope glycoprotein, HEK-293T cells (American Type Culture Collection) grown to 70–80% confluence were transfected (Geneporter transfection reagent, Gene Therapy Systems, San Diego, Calif.) with plasmids expressing secreted gp120 from HIV-1 strains ADA and HXBc2 (ref. Kolchinsky). Twenty-four hours after the transfection, the medium was replaced with labeling medium, as described above. The cell supernatants containing $^{35}$S-cysteine/methionine-labeled gp120 were harvested every 48 hours a total of three times. The labeled gp120 was purified from the pooled supernatants using a Protein A Sepharose-F105 antibody column, as described (ref. Wu et al).

Coating of Dynabeads by Antibodies and Streptavidin

Tosylactivated Dynabeads® M-280 (Dynal, Inc., Lake Success, N.Y.) were conjugated with 1D4 antibodies (National Cell Culture Center, Minneapolis, Minn.), and streptavidin (Vector Laboratories, Inc., Burlingame, Calif.) at a molar ratio 10:1 unless specifically mentioned. Approximately $6\times10^8$ beads in 1 ml volume were vortexed, pelleted on a magnetic separator (Dynal) and resuspended in 1 ml of binding buffer (0.1 M sodium phosphate, pH 7.4) containing 1 mg of 1D4 antibody and 30 µg of streptavidin. After incubation on a rocking platform for 20 hours at 37° C., the unbound surface reactive groups on the beads were inactivated by treatment with 0.2 M Tris-HCl (pH 8.5) for 4 hours at 37° C. The noncovalently absorbed proteins were removed by a one-hour incubation in medium composed of 1% cyclohexyl-pentyl- -D-maltoside (Cymal™-5) detergent (Anatrace, Maumee, Ohio), 20 mM Tris-HCl (pH 7.5), 100 mM $(NH_4)_2SO_4$ and 1M NaCl. Then the 1D4/streptavidin-beads were washed twice and stored at 4° C. in PBS. The efficiency of antibody conjugation to the beads, which was estimated by FACS using anti-mouse R-phycoerythrin-conjugated IgG (IgG-PE) (Boehringer Mannheim, Indianapolis, Ind.), was approximately $5\times10^4$ antibody molecules/bead. The 2D7/Streptavidin conjugation was accomplished using the same protocol.

Preparation of Lipid Solutions for Liposomal Membrane Reconstitution

All lipids were obtained as chloroform solutions from Avanti Polar Lipids (Alabaster, Ala.). A total of 10 mg of chloroform-dissolved lipids 1-Palmitoyl-2-Oleoyl-sn-Glycero-3-Phosphocholine (POPC), 1-Palmitoyl-2-Oleoyl-sn-Glycero-3-Phosphoethanolamine (POPE) and Dimyristoylphosphatidic acid (DMPA), mixed in a molar ratio of 6:3:1, were dried in a 2-ml polyethylene tube under a vacuum until all of the solvent was removed. One milliliter of PBS was added to the tube and a liposomal solution was obtained by 1–2 min ultrasonication in an ice bath using the Ultrasonic Processor (Heat Systems, Inc., Farmingdale, N.Y.). Liposomal solutions of total lipids from membranes of Cf2Th cells, which were extracted with chloroform/methanol (ref. Folch), were prepared similarly, using a final lipid concentration of 10 mg/ml. Liposomal solutions of the head group-modified synthetic lipids dipalmitoylphosphoethanolamine-N-Biotinyl (Biotinyl-DPPE) and dioleoylphosphoethanolamine-Lissamine Rhodamine B (Rho-DOPE), at a final concentration of 1 mg/ml, were prepared separately using the same protocol. All liposomal solutions were kept in liquid $N_2$ until use.

Formation of Proteoliposomes with Purified CCR5

Approximately $10^8$ Cf2Th/CCR5 cells were lysed in 10 ml of solubilization buffer (S-buffer) composed of 100 mM $(NH_4)_2SO_4$, 20 mM Tris-HCl (pH 7.5), 10% Glycerol, 0.5% (w/v) Cymal™-5 and Protease Inhibitor Mixture (one tablet of Complete™ (Boehringer Mannheim) per 50 ml) for 30 minutes at 4° C. Cell debris was removed by 30 min centrifugation at 150,000×g. Approximately $5\times10^8$ 1D4/Streptavidin-coated beads washed in S-buffer were added to the cleared cell lysate and incubated in it for 1 h at 4° C. on a rocking platform. The CCR5-bound beads were then removed from the cell lysate and extensively washed in S-buffer. For formation of the lipid membrane around the CCR5-containing beads, 1 mg of liposomes composed of either synthetic lipid mixtures or Cf2Th cellular lipids was combined with 10 g of liposomes made from Biotinyl-DPPE and solubilized in 1 ml S-buffer. When fluorescent labeling of the lipid membrane was desired, 10 g of Rho-DOPE was added to the mixture. This detergent-containing mixture was added to CCR5-containing beads and, after 1 hour incubation at 4° C., the detergent was slowly removed by dialysis for 24 hours at 4° C. in 12,000-kDa dialysis tubing against 100 mM $(NH_4)_2SO_4$, 20 mM Tris-HCl (pH 7.5) and 10% glycerol. The excess of unbound lipid and residual detergent was removed on a magnetic separator and proteoliposomes were stored in PBS at 4° C. for up to two months.

The protein composition of CCR5-proteoliposomes was analyzed by silver staining or, when $^{35}$S-cysteine/methionine-labeled CCR5 was used, by autoradiography. For these purposes, $10^7$ proteoliposomes were resuspended in 2% SDS-sample buffer and, after 1 hour incubation at 55° C., the eluted sample was run on an 11% polyacrylamide mini-gel under reducing conditions.

Ligand Binding to CCR5-proteoliposomes

The binding of the 2D7 anti-CCR5 antibody was analyzed by FACS and confocal microscopy, using 2D7 conjugated with R-phycoerythrin (2D7-PE). CCR5-proteoliposomes were suspended in 5% BSA fetal calf serum in PBS or, in some experiments, in binding buffer (see below) and incubated with 2D7-PE for one hour at 22° C. The proteoliposomes were then washed in the same buffer, fixed in 2% formaldehyde in PBS, and analyzed by FACS or confocal microscopy.

The binding of the HIV-1 gp120 glycoprotein to CCR5-proteoliposomes was analyzed by FACS using unlabelled gp120 (JR-FL strain) or by SDS-polyacrylamide gel analysis of bound, radiolabeled gp120 proteins. For the FACS analysis, CCR5-proteoliposomes were suspended in 0.5 ml binding buffer (150 mM NaCl, 5 mM $CaCl_2$, 2 mM MgCl2, 20 mM Tris, pH 7.5) and incubated for one hour at 22° C. with 3–5 g JR-FL gp120 or with JR-FL gp120 that had been preincubated for one hour at 37° C. with an equimolar concentration of sCD4. Afterwards, the anti-gp120 antibody C11 (kindly provided by Dr. James Robinson, Tulane University) and a fluorescein-conjugated goat anti-human IgG (Pharmingen) were added, each at a final concentration of 3–5 $\mu$g/ml. Following incubation at 22° C. for one hour, the CCR5-proteoliposomes were washed in the binding buffer, fixed in 2% formaldehyde in PBS, and used for FACS and confocal microscopy.

For the studies of radiolabeled HIV-1 gp120 binding to CCR5-proteoliposomes, the metabolically labeled gp120 glycoproteins from a CCR5-using HIV-1 strain, ADA, and from a CXCR4-using HIV-1 strain, HXBc2, were employed. The gp120 glycoproteins were incubated in either the presence or absence of sCD4 (10 nM final concentration) for one hour at 37° C. Approximately $10^7$ CCR5-proteoliposomes were resuspended in 1 ml of binding buffer and incubated with the gp120 glycoproteins for 1 hour at 22° C. The proteoliposomes were extensively washed in the binding buffer and then resuspended in SDS-sample buffer containing 5% β-mercaptoethanol. After boiling for 2 minutes, the samples were loaded on 10% polyacrylamide mini-gels and analyzed by autoradiography.

Protein Composition of CCR5-proteoliposomes

Figure 3:
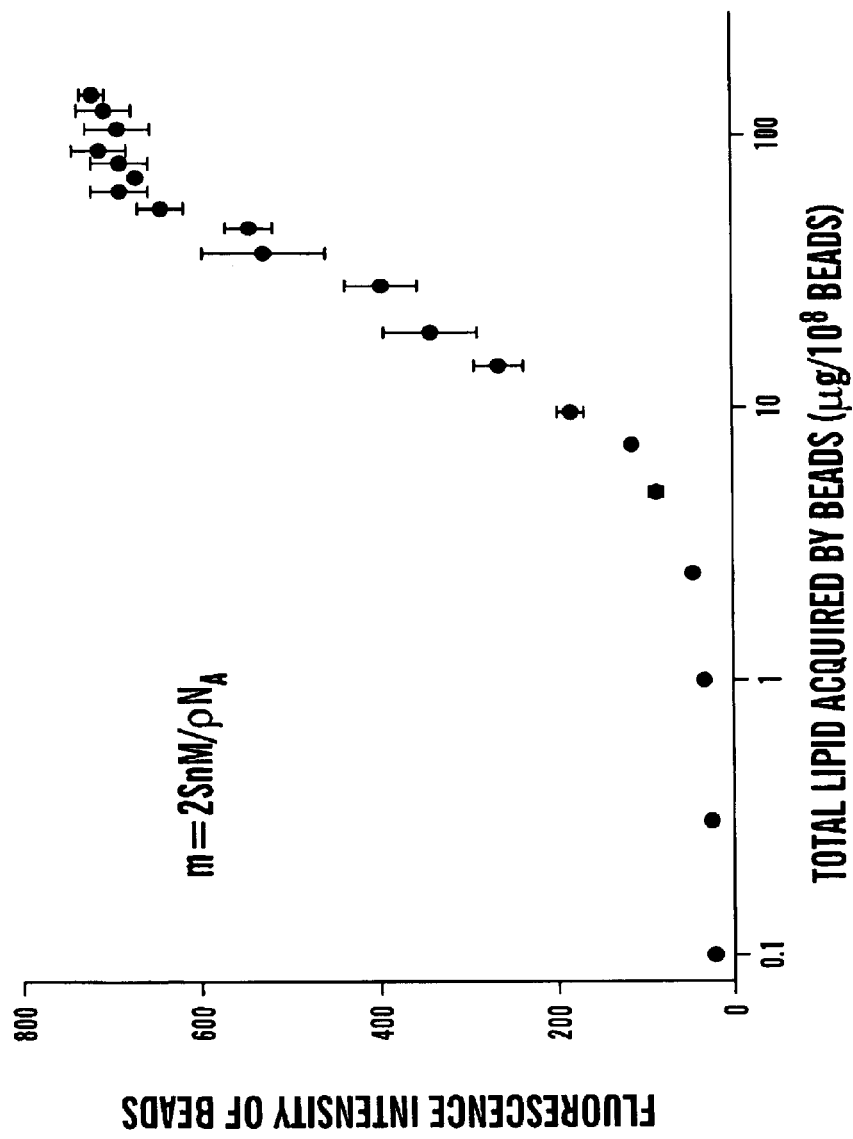
FIG. 3 shows quantitation of the lipid acquired by paramagnetic CCR5-proteoliposome beads. Approximately 10$^8$ 1D4/Streptavidin-conjugated beads were reconstituted with CCR5 and different quantities of lipids. The lipid mixtures contained POPC/POPE/DPPA in a 6:3:1 molar ratio, as well as 1% each (by weight) of biotinyl-DPPE and rhodamine-DOPE. The intensity of lissamine rhodamine B fluorescence, which was measured by FACS, exhibited a mean value of 20,000 counts. The data points shown represent the average of three independent experiments, with standard deviations indicated. In the inset is the formula by which the approximate mass of total lipid (m) necessary for complete encapsulation of given number of beads (n) by a single lipid bilayer membrane was calculated. S is the estimated effective surface of the 2.5-micrometer diameter Dynal bead. The approximate area occupied by one lipid molecule in the bilayer membrane (P) was considered to be 60 A$^2$. $N_A$ is Avogadro's number and M the average molecular weight of the lipids used for membrane reconstitution.

To examine the cellular proteins incorporated into the proteoliposomes, Cf2Th-CCR5 cells were metabolically labeled with $^{35}$S-cysteine and $^{35}$S-methionine and used for proteoliposome formation. The proteoliposomes were incubated in SDS-sample buffer at 55° C. for one hour and the labeled proteins analyzed on polyacrylamide gels (FIG. 3). Prominent bands associated with mature CCR5 (43 kDa) and a previously seen CCR5 derivative (36 kDa) were observed, as well as faint bands associated with higher-molecular weight aggregates of CCR5. Other cellular proteins were apparently present at only trace levels. These results indicate that CCR5 is the major cellular protein in the proteoliposomes.

The proteins in the paramagnetic proteoliposomes were also examined by silver staining of polyacrylamide gels of the SDS lysates. The only other bands visible in addition to the CCR5 bands described above were those associated with the 1D4 antibody heavy and light chains (55 and 25 KDa, respectively) and streptavidin (60 KDa) (data not shown). This demonstrates that apparently, no cellular proteins other than CCR5 are incorporated stoichiometrically into the paramagnetic proteoliposomes.

Analysis of the Lipid Bilayer Membrane in CCR5-proteoliposomes

Figure 4:
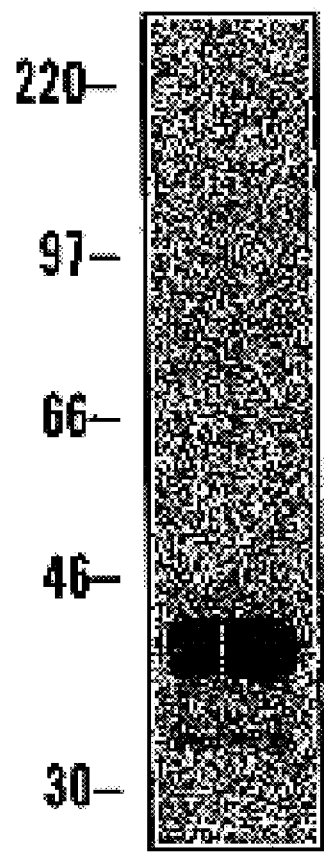
FIG. 4 shows cellular protein composition of CCR5-proteoliposomes. The $^{35}$S-cysteine/methionine-labeled lysate from Cf2Th-CCR5 cells was used for CCR5-proteoliposome formation. Approximately 3×10$^7$ CCR5-proteoliposomes were incubated with SDS-sample buffer for 1 hour at 55° C. prior to loading on an 11% SDS-polyacrylamide mini-gel, which was ran under reducing conditions. The gel was treated for 1 hour with Enhance (NEN), dried and autoradiographed.

The total quantity of lipid incorporated into the proteoliposomes was determined. FACS analysis of CCR5-proteoliposomes formed with increasing amounts of lipid containing 1% rhodamine-DOPE revealed that approximately 80–90 $\mu$g of lipid was acquired per $10^8$ beads (FIG. 4). This is higher than the amount of lipid (approximately 40 $\mu$g) that is theoretically needed to form bilayers surrounding beads of 2.8 $\mu$m diameter (see formula in FIG. 4, inset). This difference can be explained by the irregularity of the bead surface, which was documented by scanning electron microscopy (data not shown), and which could contribute to the formation of small micelle-like structures in the crevasses of the bead surface. Additionally, some of the input lipid may have been lost during dialysis.

Figure 5A:
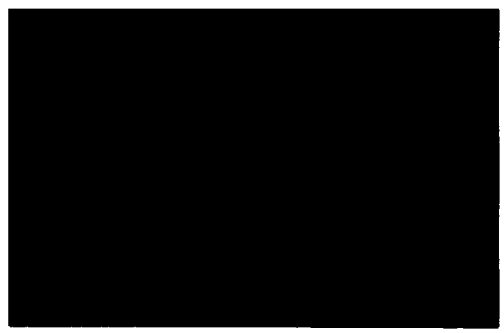
FIGS. 5A–F show confocal microscopy of fluorescently labeled CCR5-proteoliposomes. Excluding the control beads (FIG. 5A), all beads were reconstituted with POPC/POPE/DMPA lipid mixture (in a 6:3:1 molar ratio) containing 1% Biotinyl-DPPE.
Figure 5B:
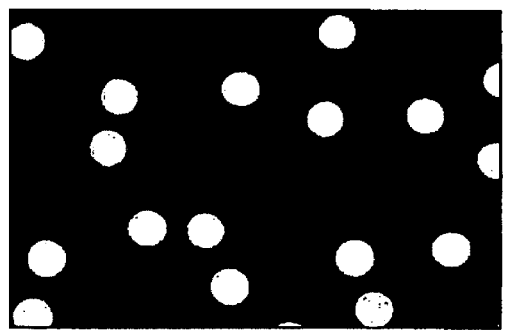

The CCR5-proteoliposomes were also studied by confocal microscopy (FIGS. 5A and 5B). The control paramagnetic beads did not exhibit fluorescence indicative of rhodamine-DOPE incorporation. By contrast, the CCR5-proteoliposomes that had been formed with 1% rhodamine-DOPE fluoresced intensely and uniformly. No lipid vesicles or other structures greater than 0.1 $\mu$m were observed on the surface of the fluorescently labeled CCR5-proteoliposomes. These data are consistent with the CCR5-proteoliposomes being surrounded by a single lipid bilayer membrane with at most small irregularities.

Ligand Binding Properties of CCR5-proteoliposomes

Figure 5C:
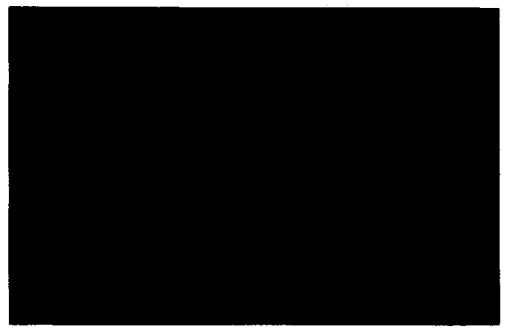
Figure 5D:
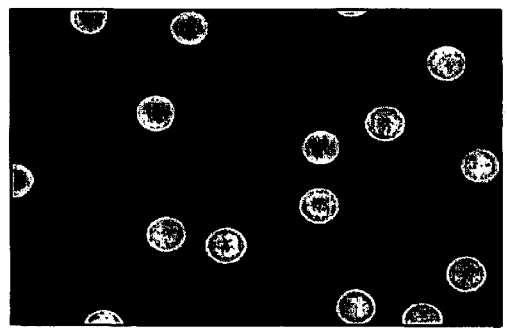

CCCR5-proteoliposomes efficiently bound the 2D7 antibody, which recognizes a conformation-dependent epitope on the CCR5 ectodomain (FIGS. 5C and 5D).

Figure 5E:
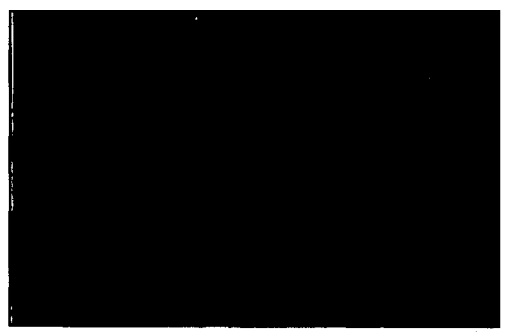
Figure 5F:
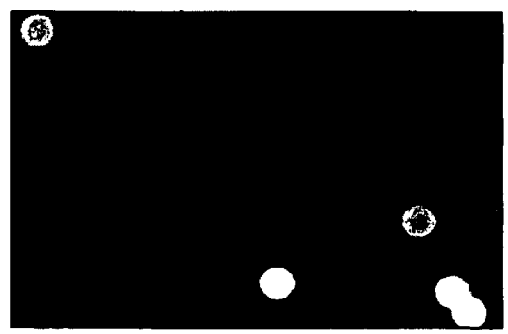

To examine the ability of the CCR5-proteoliposomes to bind the HIV-1 exterior envelope glycoprotein, the gp120 glycoprotein from the CCR5-using strain JR-FL was preincubated with a soluble form of CD4 (sCD4) to induce the high-affinity interaction with CCR5. The gp120/sCD4 complex was incubated with CCR5-proteoliposomes, after which the bound complexes were detected by the C11 anti-gp120 antibody. Binding of the gp120 glycoprotein/sCD4 complexes to the CCR5-proteoliposomes, but not to control proteoliposomes lacking CCR5, was readily detected (FIGS. 5E and 5F).

Figure 6A:
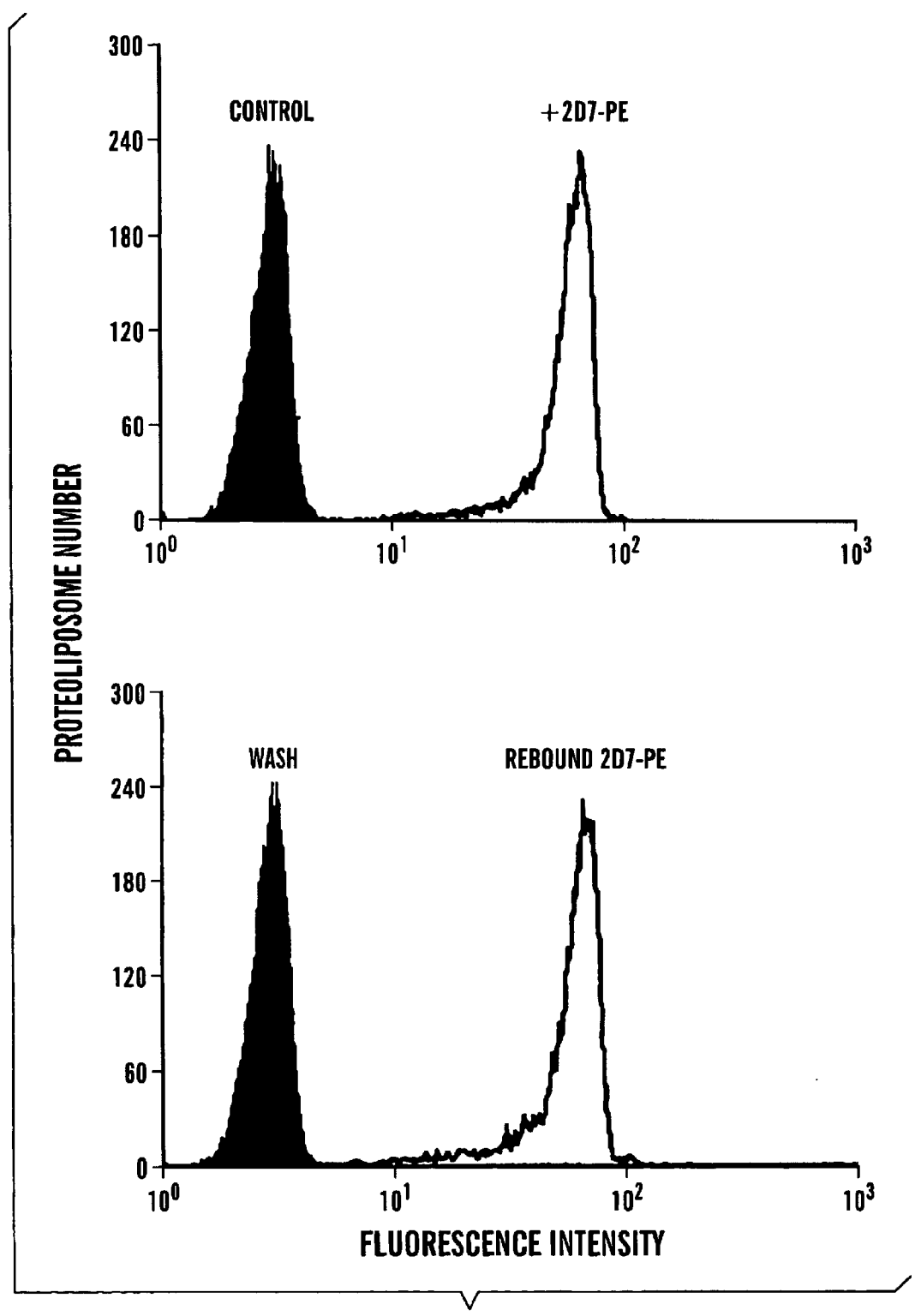
FIGS. 6A and 6B show the ligand-binding properties of CCR5-proteoliposomes.
Figure 6B:
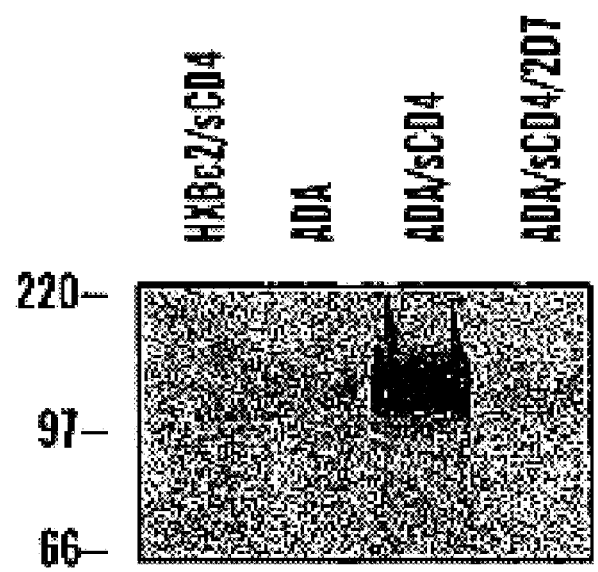
Figure 7:
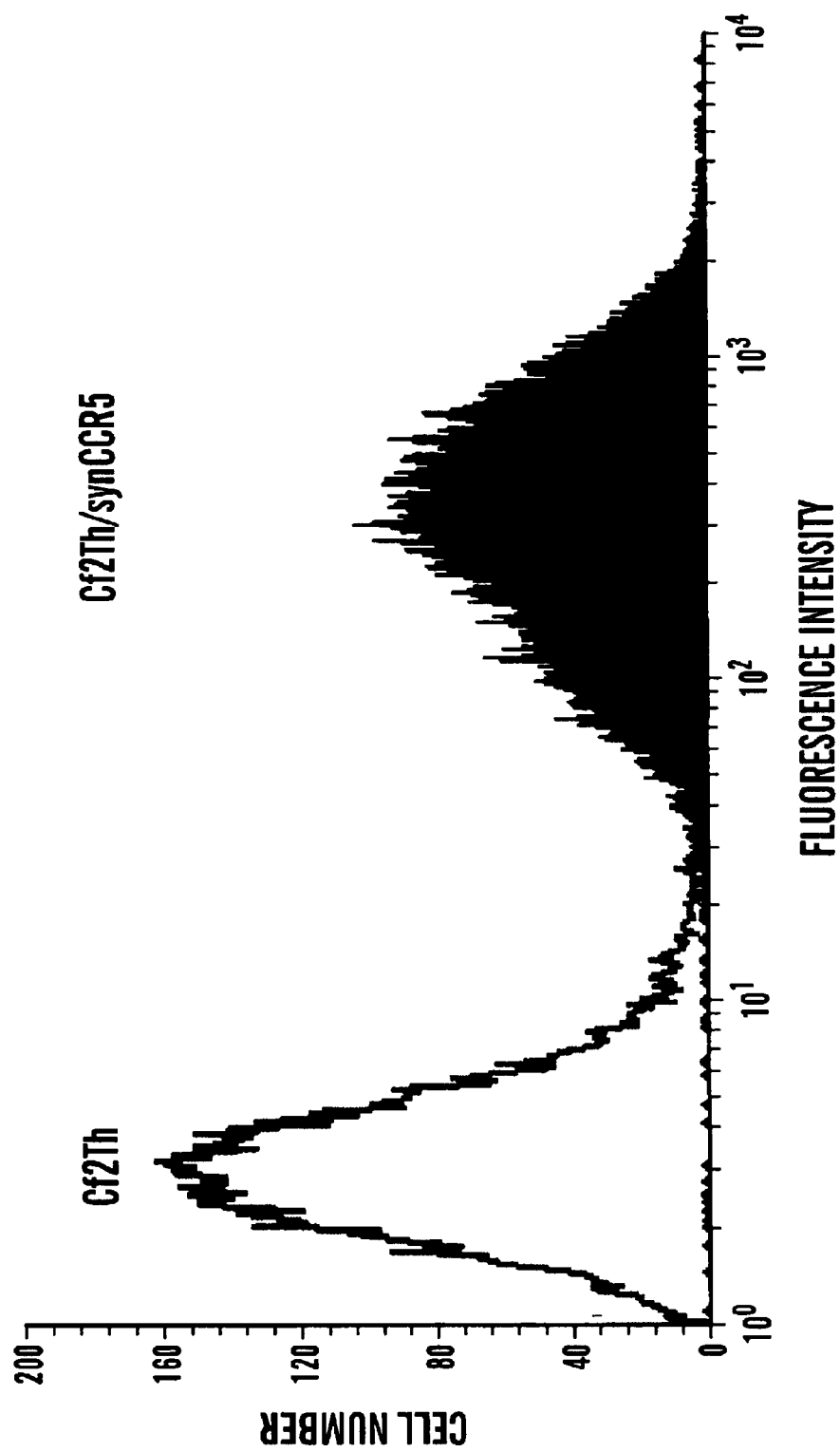
FIG. 7 is a FACS analysis of Cf2Th cells, with or without synCCR5.
Figure 8A:
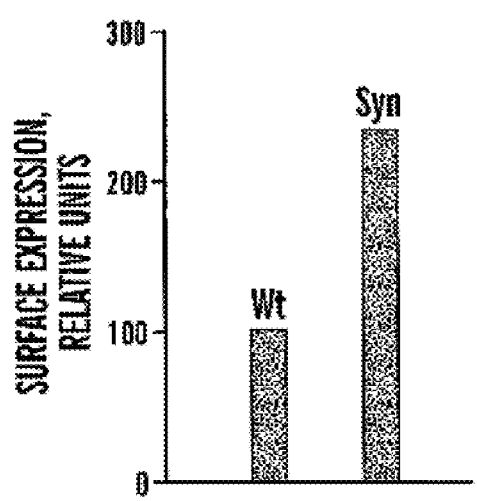
FIGS. 8A–D show expression of CCR5.
Figure 8B:
Figure 8C:
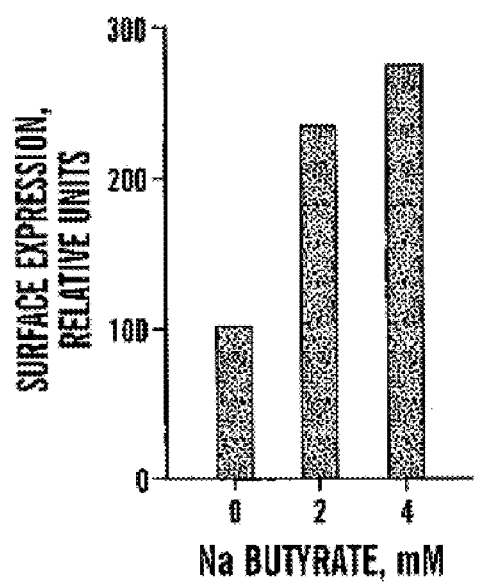
Figure 8D:
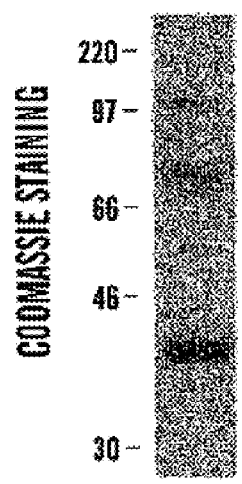
Figure 9:
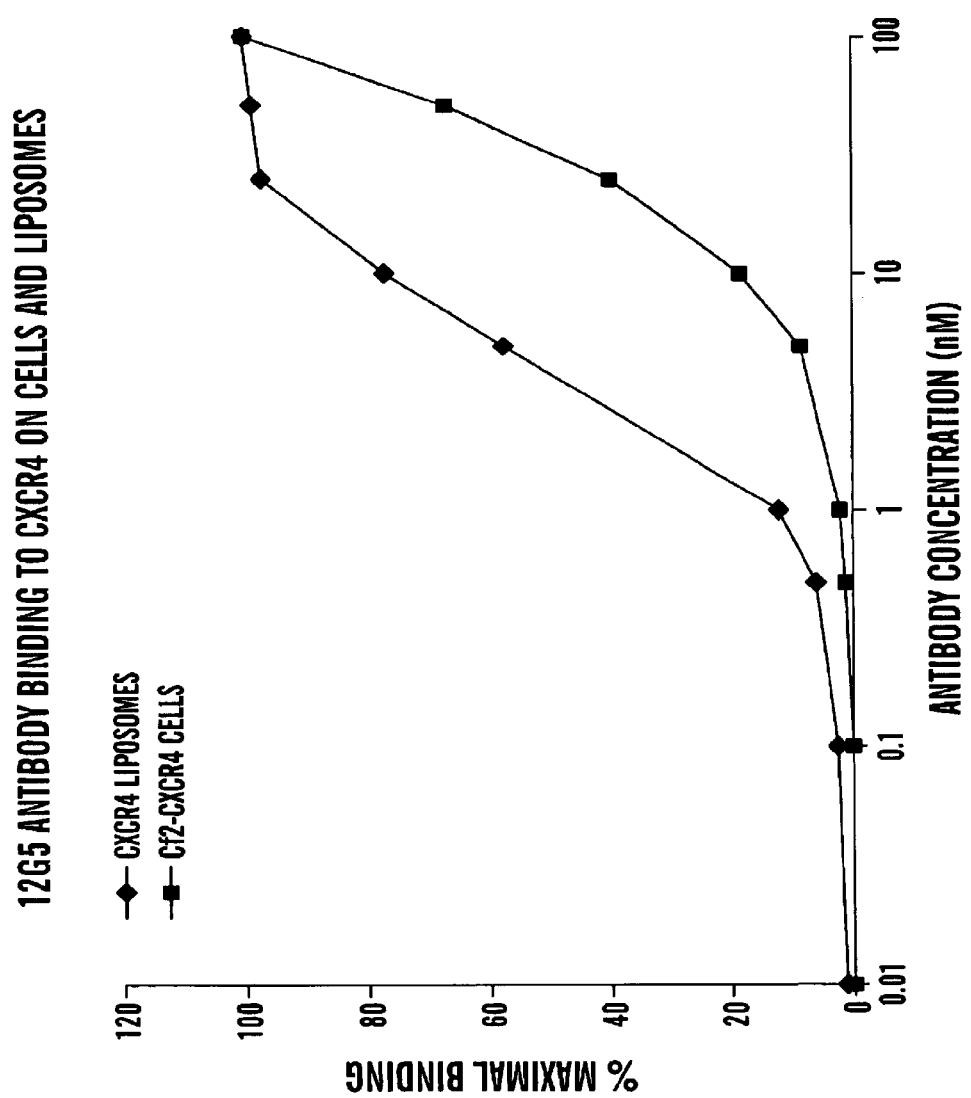
FIG. 9 shows binding of the 12G5 antibody to CXCR4-proteoliposomes and to CXCR4-expressing cells. CXCR4-proteoliposomes were prepared as described in the text from cells expressing human CXCR4 with a C-terminal C9 tag. The binding of the 12G5 antibody, which recognizes a conformation-dependent structure on CXCR4, to the CXCR4-expressing cells and CXCR4-proteoliposomes is shown. The apparent affinity of the 12G5 antibody for the CXCR4 on the proteoliposome surface is at least as good as that for CXCR4 on cells. A similar result was obtained for the conformation-dependent, CXCR4-directed antibody FAB173 (data not shown).

The binding of the HIV-1 gp120 glycoprotein to the CCR5-proteoliposomes was also examined in a different assay. Equivalent amounts of metabolically labeled gp120 glycoproteins from an HIV-1 strain, HXBc2, which does not use the CCR5 protein as a coreceptor, and from the ADA strain, which uses CCR5 as a coreceptor, were added to the CCR5-proteoliposomes. Only the ADA gp120 glycoprotein detectably bound the CCR5-proteoliposomes (FIG. 6A). This binding was enhanced by the addition of sCD4. The binding of the ADA gp120/sCD4 complex to the CCR5-proteoliposomes was inhibited by preincubation of the proteoliposomes with the 2D7 anti-CCR5 antibody. These results indicate that the gp120 glycoprotein from a CCR5-using HIV-1 specifically binds CCR5 in the proteoliposome, and that CD4 binding enhances the gp120-CCR5 interaction, as has been observed with cell surface CCR5 (Wu, L. et al. (1996) Nature 384: 179–183; Trkola, A. et al. (1996), Nature 384: 184–187).

Stability of CCR5-proteoliposomes

The effects of alterations in pH, ionic strength and temperature on the stability of the CCR5-proteoliposomes were examined. Rhodamine-DOPE-labeled CCR5-proteoliposomes were exposed to acidic (pH=3) or basic (pH=10) conditions for 30 minutes, after which they were returned to a neutral pH environment. The fluorescence intensity measured by FACS was comparable to that observed for untreated control CCR5-proteoliposomes (data not shown). Fluorescence intensity was also not affected by incubation in solutions of different ionic strengths, ranging from less than 1 mM to 3M NaCl (data not shown). The binding of the 2D7 antibody to CCR5-proteoliposomes was completely disrupted by incubation of the antibody-proteoliposome complex at pH 3.0 for 30 minutes (FIG. 5B). However, the ability of the 2D7 antibody to rebind the CCR5-proteoliposomes was completely restored by returning the pH to 7.0. The CCR5-proteoliposomes were stable at temperatures up to 50° C. for short periods of time (less than two hours) and could be stored for at least two months in PBS at 4° C. without loss of binding properties.

We have thus shown that an integral membrane protein such as the GPCR CCR5 can be expressed at reasonably high levels in mammalian cells and purified in its native state in detergent-containing solutions. We have shown that the purified CCR5 can be reconstituted into a native lipid membrane environment formed on the surface of paramagnetic beads. Accordingly, with minor adjustments, the approach is applicable to many integral membrane proteins.

Example 2

Proteoliposomes Containing CXCR4

Purification of CXCR4 Proteoliposomes

CXCR4-Cf2Th cells were grown to full confluency in 100 mm cell culture dishes. Cells were detached from the dish with 1×PBS/5 mM EDTA and pelleted in microcentrifuge tubes at $1 \times 10^8$ cells/pellet. The pellet was resuspended in an ice cold buffer containing 100 mM (NH4)2SO4, 20 mM Tris pH 7.5, 20% glycerol, 1× Complete (Roche) protease inhibitor cocktail and 1% of either CHAPSO (Anatrace) or Cymal-7 (Anatrace). Resuspended cells were incubated for 5 minutes on ice followed by 25 minutes at 4° C. on a Nutator (Fisher Scientific). After incubation, cell debris was removed by centrifugation at 14,000×g for 30 minutes at 4° C. The supernatant was transferred to a new microcentrifuge tube and $5 \times 10^8$ 1D4 conjugated M-280 Dynal beads were added. Cell lysate was incubated with beads for 2.5 hours at 4° C. on a Nutator. The tube was then placed in a Dynal MPC-S magnet to remove the beads. The beads were washed two times with ice cold washing buffer (either 1% CHAPSO or Cymal-7, 100 mM $(NH4)_2SO_4$, 20 mM Tris pH 7.5 and 20% glycerol). After washing, beads prepared with CHAPSO were resuspended in 2.5 ml of ice cold CHAPSO washing buffer containing 1.5 mg 1-Palmitoyl-2-Oleoyl-sn-Glycero-3-Phosphocholine, 0.75 mg 1-Palmitoyl-2-Oleoyl-sn-Glycero-3-Phosphoethanolamine, 0.225 mg 1.2 Dioleoyl-sn-Glycero-3-Phosphate and 0.025 mg Biotinyl-Phosphoethanolamine. Cymal-7 prepared beads were resuspended in ice cold 1% Cymal-5 washing buffer containing the above described lipids. The solution was then injected into a Slide-A-Lyzer (Pierce, 10 kDMWCO) and dialyzed for 24 hours against washing buffer containing no detergent at 4° C. The samples were dialyzed in a specially designed machine that constantly rotated the Slide-A-Lyzer to prevent settling of the beads. Following dialysis, the paramagnetic proteoliposomes were removed from the Slide-A-Lyzer and washed two times in 1×PBS/2% FBS to remove unbound lipid and any remaining detergent. Proteoliposomes were stored in 1×PBS/2% FBS/0.02% sodium azide for up to two months at 4° C.

Example 3

Proteoliposomes Containing gp160

Construction and Expression of gp160

We have produced solid phase paramagnetic gp120-gp41 proteoliposomes by the following methodology. HIV-1 envelope glycoproteins derived from the YU2 HIV-1 primary isolate were transiently expressed in 293T cells from the pSVIII expression plasmid. The glycoproteins were rendered cleavage-defective by two R-to-S amino acid changes adjacent to the gp120-gp41 cleavage site to generate gp160 cleavage defective glycoproteins. The glycoproteins were further modified by truncation of the cytoplasmic tail, which increased cell surface expression several fold (data not shown), and by the addition of a C-terminal C9 epitope tag derived from the C-terminus of rhodopsin.

Preparation of gp160 Proteoliposomes

Figure 11:
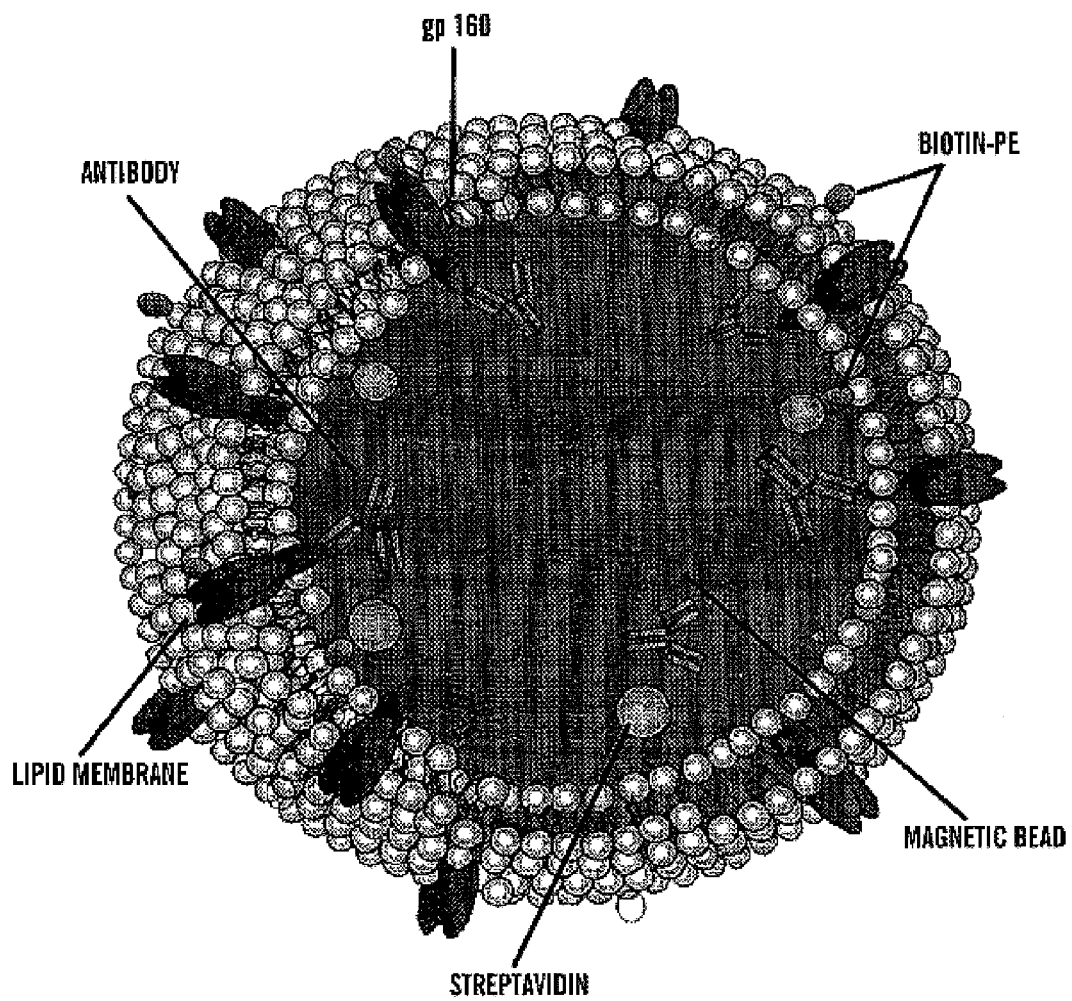
FIG. 11 shows a schematic representation of the reconstituted gp160 proteoliposomes.

Cells expressing the gp160 glycoproteins on their cell surface were lysed in buffer containing 1% Cymal-5 detergent. The proteins were then captured on paramagnetic, tosyl-activated Dynal beads that had been covalently coupled with the C9-specific murine antibody, 1D4. During the procedure, streptavidin was also simultaneously coupled to the bead at a molar ratio of IgG to streptavidin of 10:1. Following several washes in lysis buffer, the affinity-captured proteins were dialyzed against PBS in the presence of polar lipids. The lipid mixture contained 1% biotinylated lipids to permit attachment to the streptavidin derivatized on the surface of the bead. This process was designed to nucleate an anchored, reconstituted lipid bilayer surrounding the bead and surrounding the transmembrane region of the gp160 molecules. A schematic of the gp160 proteoliposomes is shown in FIG. 11.

Protein and Lipid Bilayer Membrane Composition of gp160 Proteoliposomes

Figure 10:
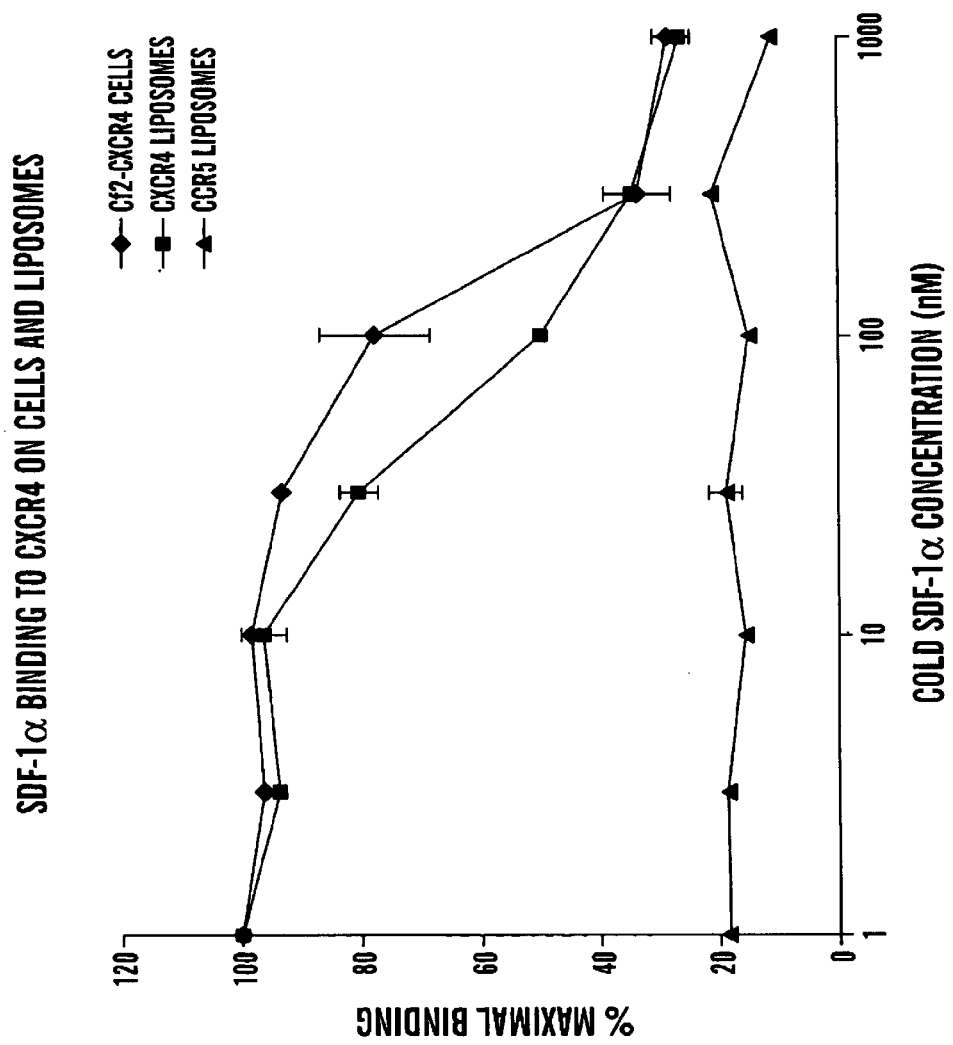
FIG. 10 shows binding of SDF-1α to CXCR4 on cells and proteoliposomes. Radiolabeled SDF-1α, the natural CXCR4 ligand, was incubated with either CXCR4-expressing cells or proteoliposomes bearing CXCR4 or CCR5. Unlabeled (cold) SDF-1α was added in increasing amounts, and the amount of radiolabeled SDF-1α bound to the cells or proteoliposomes was measured. The SDF-1α bound with high affinity to the CXCR4-expressing cells and CXCR4-proteoliposomes, but not to the CCR5-proteoliposomes.
Figure 12A:
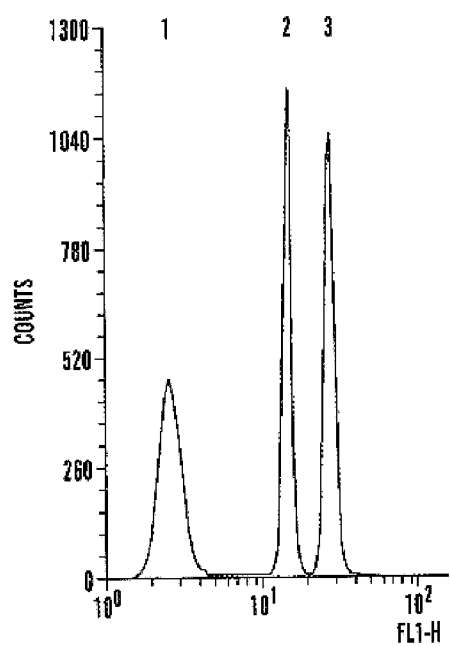
FIGS. 12A–B show analysis of the gp160 proteoliposomes.
Figure 12B:
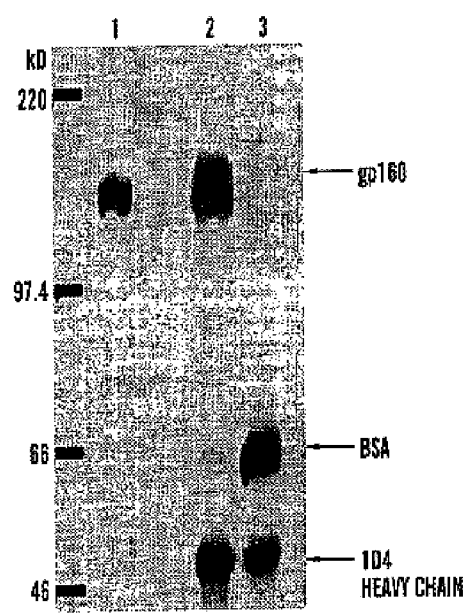
Figure 13:
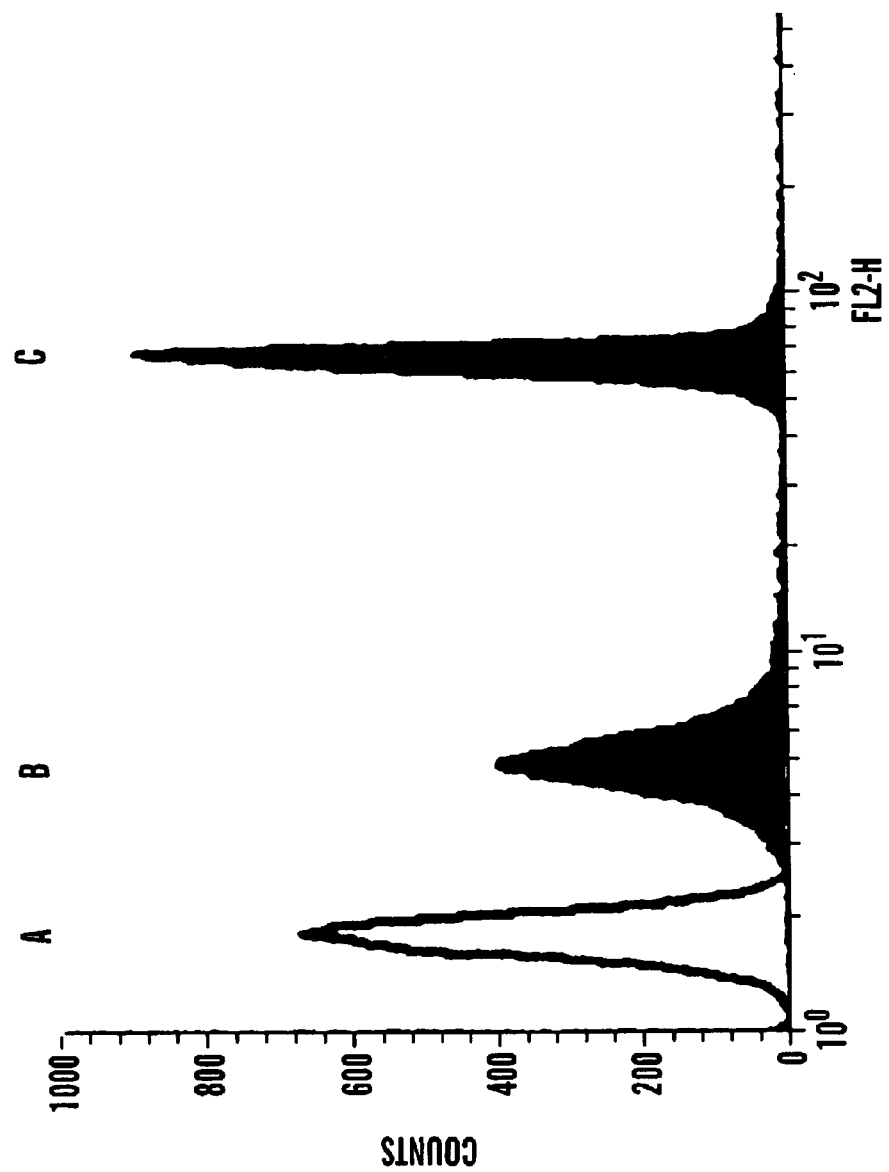
FIG. 13 shows FACS analysis of proteoliposomes with and without a reconstituted membrane. Peak A is a gp160 proteoliposome control stained with a-human-FITC; Peak B is gp160 proteoliposomes with a reconstituted membrane stained with a-mouse IgG-PE; Peak C is gp160 glycoproteins on beads without membrane, stained with a-mouse IgG-PE.
Figure 14A:
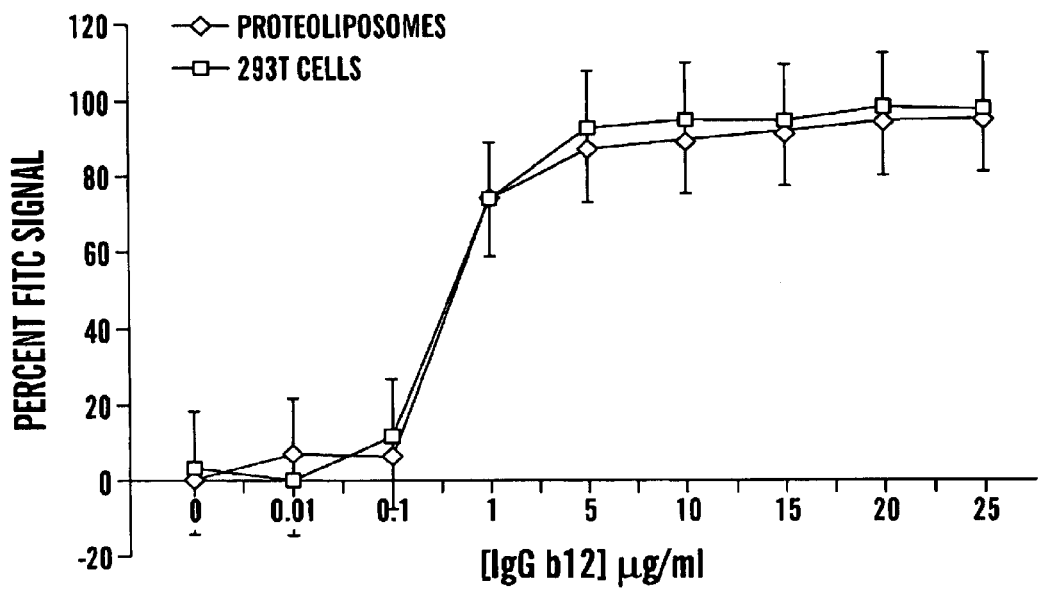
FIGS. 14A–B show FACS-generated binding curves.
Figure 14B:
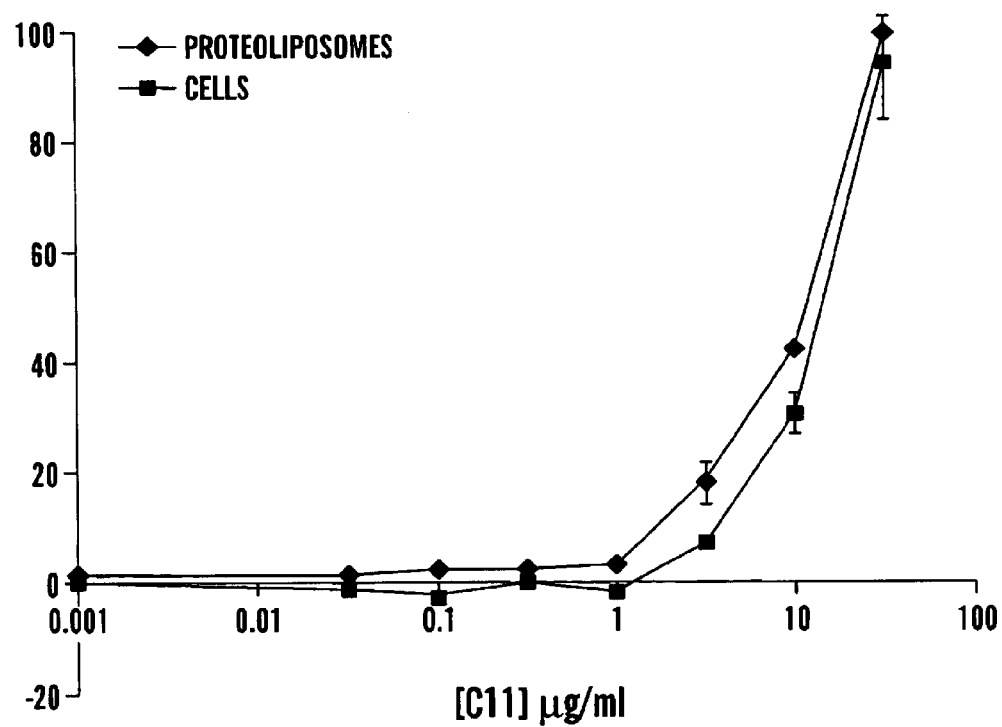

We have performed considerable analysis of the gp160 proteoliposomes to confirm that both the gp160 molecules were captured in a native condition and that a lipid membrane was indeed reconstituted on the bead surface. The beads were analyzed by FACS to confirm that the gp160 oligomers were detectable on the surface of the beads by both AIDS patient sera, by the CD4BS antibody IgGb12, several other conformationally-sensitive monoclonal antibodies and by CD4-IgG (FIG. 10A and data not shown). The AIDS patient sera recognized the gp160 on the surface more efficiently that any individual monoclonal antibody (FIG. 12A). This effect is likely due to the polyclonal mixture of the anti-gp160 antibodies present in the serum that recognizes many envelope-specific epitopes. We also confirmed that the captured gp160 glycoproteins were relatively pure by boiling and reduction of the reconstituted gp160 proteoliposomes and analyzing the protein content of the beads on SDS Polyacrylamide gels (FIG. 12B).

Figure 16:
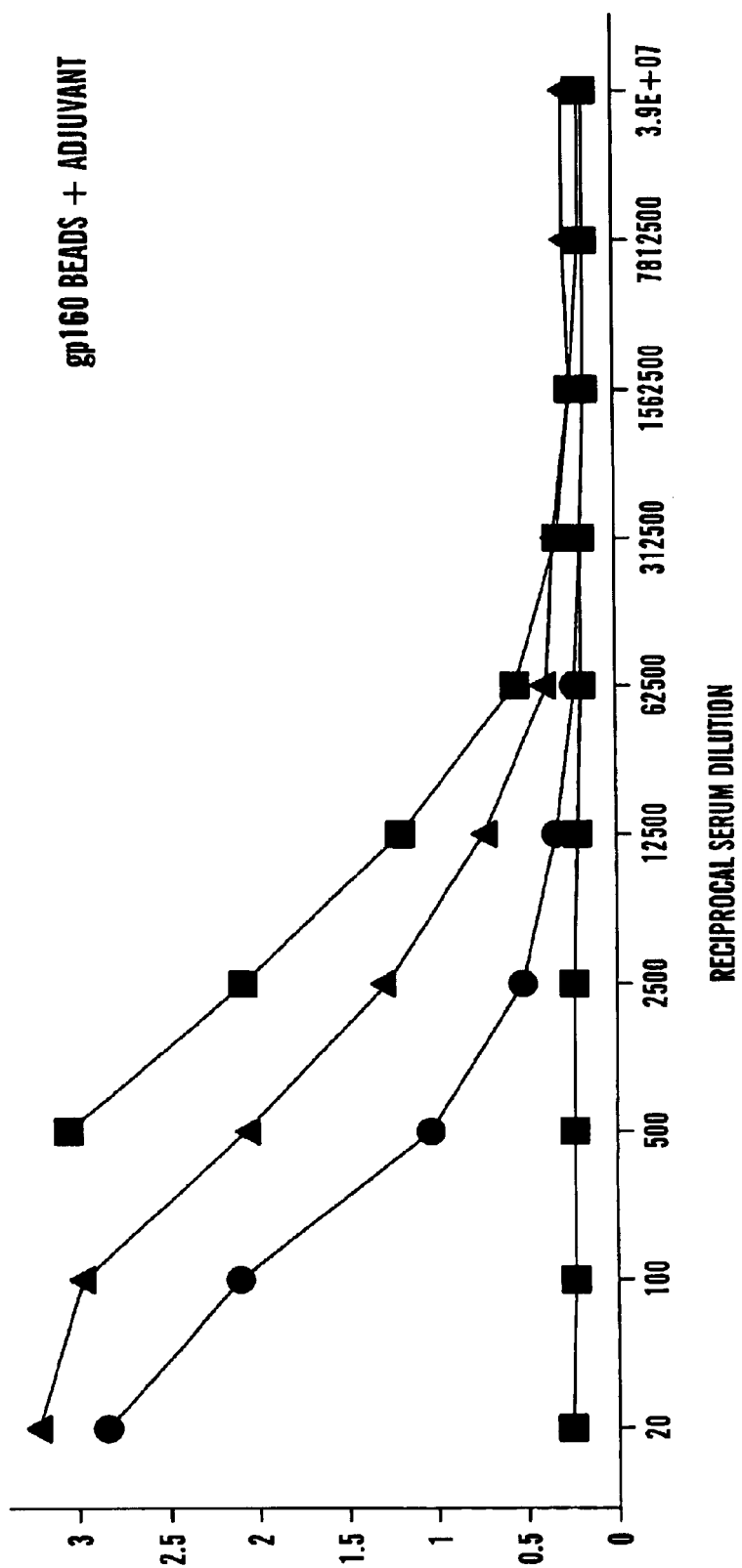
FIG. 16 shows an ELISA of sera from gp160 proteolipsome-immunized mice and control sera. Prebleed sera was used as negative control sera; PADRE serum refers to mice previously immunized with gp120-PADRE glycoproteins that served as a positive control.

We confirmed that the lipid bilayer was reconstituted by visualizing the incorporation of rhodamine-conjugated lipid (rhodamine-DOPE) into the proteoliposome membrane utilizing fluorescent microscopy (FIG. 16). Without prior membrane reconstitution of the beads, there was undetectable fluorescent staining of the beads by the rhodamine-DOPE (data not shown).

In addition, beads containing captured gp160 glycoproteins either with or without a reconstituted membrane were probed with an anti-mouse IgG secondary antibody to determine if the membrane would impede access of the secondary antibody to the 1D4 murine antibody conjugated to the bead. The PE-conjugated secondary antibody recognized the beads containing a reconstituted membrane to a significantly lower degree than gp160 beads lacking a membrane when analyzed by FACS (FIG. 11, peak B compared to peak C). We interpreted these data to mean that a membrane had been reconstituted around the surface of the bead to a significant degree.

To confirm that the conformation of the gp160 oligomers was not altered from that on the cell surface by the proteoliposome capture and reconstitution procedure, we have performed a comparative binding study by FACS. By this analysis, the recognition of the oligomeric envelope glycoproteins by IgGb12 was equivalent on either the cell surface or on the surface of the gp160-proteoliposomes (FIG. 12A). Half-maximal binding of the IgGb12 antibody was achieved at a concentration below 1 $\mu$g/ml of antibody. This concentration is consistent with previous estimates of IgG b12 affinity to be in the low nanomolar range for the highly neutralization-resistant YU2 virus (Burton et al., *Science* (1994) 266: 1024–1027). In contrast, the non-neutralizing C1/C5 conformational antibody, C11, required at least 10- to 15-fold higher concentrations to achieve an estimated half-maximal binding (FIG. 12B). This may be an underestimate of the antibody concentration required to achieve half-maximal binding since saturation binding was not achieved in this particular experiment. In any case, these results highlight the fact that the proteoliposomes behave in a manner consistent with the assertion that the gp160 glycoproteins are in a native conformation on the bead surface relevant to the conformation of envelope glycoproteins on the virus.

Example 4

Screening a Phage Display Library with Proteoliposomes Containing gp160

The defined, reconstituted gp160-proteoliposomes were used to pan a highly complex, human single-chain antibody phage display library generated in the laboratory of Dr. Wayne Marasco at the Dana-Farber Cancer Institute. After four rounds of panning, 96 clones were analyzed; 87 of the 96 clones were specific for gp120 as determined by ELISA (data not shown). The 9 non-reactive clones may represent oligomer specific antibodies or irrelevant reactivities. To confirm that the isolated phage possessed single-chain antibodies specific for gp160, FACS analysis was performed on cells expressing gp160 comparing anti-gp120 specific serum with the bacterial supernatant, an mouse anti-M13 phage IgG and anti-mouse-PE (FIG. 15). Further analysis of the soluble phage displayed single-chain antibodies is ongoing to determine their specificity. In any case, these intriguing preliminary data demonstrate the potential of the gp160-proteoliposomes to select and possibly elicit unique envelope-directed reactivities.

Example 5

Antibodies to Proteoliposomes Containing gp160

To confirm that the gp160 proteoliposomes could elicit envelope glycoprotein-specific antibodies, Balb/c mice were immunized IP with $5 \times 10^7$ proteoliposomes. By gel analysis, we estimated that each mouse received 1–2 $\mu$g of envelope glycoprotein per inoculation. To insure that the adjuvant would not disrupt the integrity of the reconstituted membrane, we preimmunized experimental mice IP with Ribi adjuvant 24 hours prior to inoculation of the beads. Subsequently we have performed membrane stability studies by incubation of rhodamine-DOPE-stained gp160 proteoliposomes in Ribi adjuvant for 2 and 24 hours. The beads were visualized by fluorescent microscopy and no decrease in the rhodamine-DOPE signal was observed on beads exposed to adjuvant (data not shown). Additional mice can be immunized with beads in Ribi adjuvant by various routes to optimize quantitative antibody responses.

Figure 17A:
FIGS. 17A–B show fluorescent microscopic pictures of gp160 proteoliposomes.
Figure 17B:
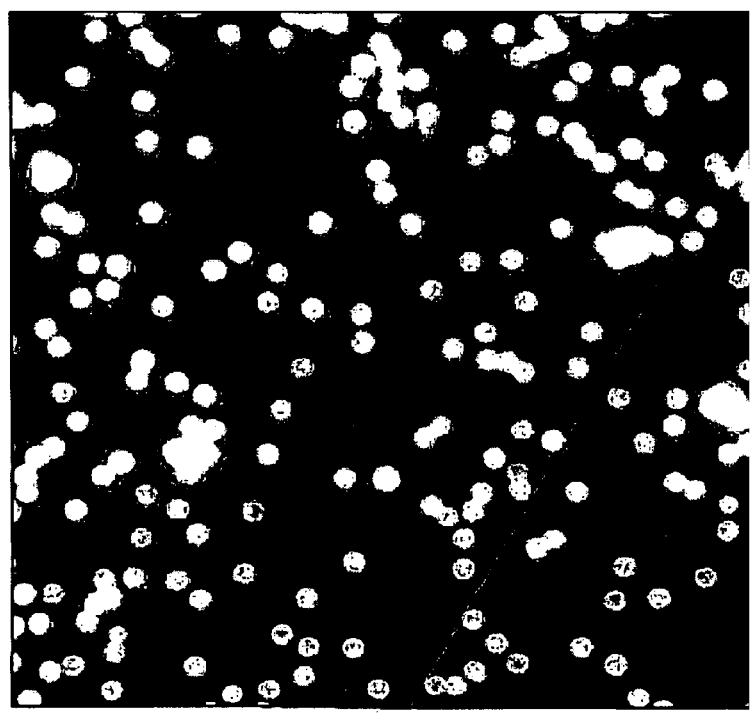

For the initial study, 2 $\mu$g of monomeric YU2 gp120 in Ribi adjuvant was used as a positive control and membrane-reconstituted beads lacking gp160 glycoprotein were used as negative controls. After 3 inoculations, we have detected anti-gp120 antibodies in the sera of the mice from both the monomeric gp120 control group and the gp160 bead group, but not from the sera of negative control mice (FIG. 17). This study demonstrates the feasibility of utilizing the gp160 proteoliposomes as immunogens to determine if they better elicit neutralizing antibodies or can elicit trimer-specific antibodies that can be isolated and characterized by monoclonal analysis. Such reagents are invaluable tools for the further elucidation of HIV-1 envelope glycoprotein higher-order structure.

All references described herein are incorporated by reference.

We claim:

1. A stable proteoliposome comprising:
   a substrate that is spherical or elliptoid in shape, wherein a ligand to a site in an integral membrane protein is anchored to said substrate, and wherein said substrate surface is surrounded by (1) a lipid membrane and (2) an isolated integral membrane protein bound to said ligand, wherein at least one transmembrane domain of said integral membrane protein present in said lipid membrane, and wherein said integral membrane protein has a wild-type conformation and is stable for at least one day.

2. The stable proteoliposome of claim 1, further comprising an attractant coating said substrate surface, and a lipid solution containing a moiety that binds to said attractant forming a lipid membrane surrounded substrate.

3. The stable proteoliposome of claims 1 or 2, wherein said integral membrane protein has at least two transmembrane domains.

4. The stable proteoliposome of claim 2, wherein the attractant is streptavidin or avidin and said moiety is biotin.

5. The stable proteoliposome of claim 4, wherein said ligand is an antibody to said integral membrane protein.

6. The stable proteoliposome of claim 5, wherein said lipid membrane is a lipid bilayer.

7. The stable proteoliposome of claim 4, wherein said integral membrane protein has at least two transmembrane domains.

8. The stable proteoliposome of claim 5 or claim 7, wherein the integral membrane protein is selected from the group consisting of G protein-coupled receptors, ion channels, amino acid transporters, glucose transporters, phosphate transporters, chemotaxis receptors, connexins, chloride channels and cystic fibrosis transmembrane conductance regulators.

9. The stable proteoliposome of claim 8, wherein said integral membrane protein is a G protein-coupled receptor.

10. A method of preparing a stable proteoliposome comprising:
   a) isolating an integral membrane protein from a cell expressing said integral membrane protein with a detergent under conditions that maintain the wild-type conformation of said integral membrane protein;
   b) adding said detergent containing said isolated integral membrane protein to a substrate that is spherical or elliptoid in shape, wherein said substrate has a ligand to a site in said integral membrane protein anchored to said substrate surface;
   c) adding a lipid solution to the substrate of step (b) to form a lipid membrane surrounded substrate; and
   d) removing said detergent from the lipid membrane surrounded substrate of step (c) under conditions that do not change said wild-type conformation of said integral membrane protein, wherein said integral membrane protein is stable for a period of at least one day.

11. The method of claim 10, wherein said substrate is coated with an attractant, wherein a moiety in said lipid solution binds to said attractant, forming a lipid membrane surrounded substrate.

12. The method of claim 10, wherein said integral membrane protein has at least two transmembrane domains.

13. The method of claim 10, 11 or 12, wherein said ligand is an antibody.

14. The method of claim 10, 11 or 12, wherein said detergent is selected from the group consisting of CHAPSO, alkyl glucopyranosides, alkyl sucroses, digitonin, hydroxyethylglucamides, oligo ethyleneglycol derivatives, dodecylmaltopyranoside and phenyl poly oxethylenes.

15. The method of claim 11, wherein said attractant is streptavidin or avidin and said moiety in the lipid solution contains biotin.

16. The method of claim 15, wherein said detergent is selected from the group consisting of cyclohexyl-pentyl-$\beta$-D-maltoside, cyclohexyl-hexyl-$\beta$-D-maltoside, and cyclohexyl-heptyl-$\beta$-D-maltoside.

17. The method of claim 16, wherein said integral membrane protein is a G protein-coupled receptor.

18. The stable proteoliposome of claim 1 or 2, wherein said integral membrane protein is stable for a period of at least one week.

19. The stable proteoliposome of claim 1 or 2, wherein said integral membrane protein is stable for a period of at least one month.

20. The stable proteoliposome of claim 1 or 2, wherein said integral membrane protein is stable for a period of at least two months.

21. The method of claim 10, wherein said integral membrane protein is stable for a period of at least one week.

22. The method of claim 10, wherein said integral membrane protein is stable for a period of at least one month.

23. The method of claim 10, wherein said integral membrane protein is stable for a period of at least two months.

24. The stable proteoliposome of claim 1 or 2, wherein said integral membrane protein has its wild type orientation, with the extracellular portion of the integral membrane protein on the surface of the proteoliposome.

25. The method of claim 10, wherein said integral membrane protein has its wild type orientation, with the extracellular portion of the integral membrane protein on the surface of the proteoliposome.

* * * * *